United States Patent
Chiao et al.

(10) Patent No.: US 9,334,480 B2
(45) Date of Patent: May 10, 2016

(54) COMPOUNDS FOR IMPROVED STEM CELL DIFFERENTIATION INTO HEPATOCYTES

(71) Applicant: Hoffmann-La Roche Inc., Nutley, NJ (US)

(72) Inventors: Eric Chiao, Chatham, NJ (US); Matthew Michael Hamilton, Hackettstown, NJ (US); Sei Kameoka, Montclair, NJ (US); Brian Leonard, Weehawken, NJ (US); Miriam Triyatni, Montclair, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 7 days.

(21) Appl. No.: 14/205,893

(22) Filed: Mar. 12, 2014

(65) Prior Publication Data

US 2015/0197726 A1    Jul. 16, 2015

Related U.S. Application Data

(60) Provisional application No. 61/792,019, filed on Mar. 15, 2013, provisional application No. 61/811,155, filed on May 22, 2013.

(51) Int. Cl.
| | | |
|---|---|---|
| *C12N 5/00* | (2006.01) | |
| *C12N 5/071* | (2010.01) | |
| *C07D 401/04* | (2006.01) | |

(52) U.S. Cl.
CPC .............. *C12N 5/067* (2013.01); *C07D 401/04* (2013.01); *C12N 2500/46* (2013.01); *C12N 2503/02* (2013.01); *C12N 2506/45* (2013.01)

(58) Field of Classification Search
None
See application file for complete search history.

(56) References Cited

PUBLICATIONS

Li et al., "Identification of 1-isopropylsulfonyl-2-amine benzimidazoles as a new class of inhibitors of hepatitis B virus," European Journal of Medicinal Chemistry 42 (2007) 1358-1364.
Ying Li et al., "Inhibition of hepatitis B virus gene expression and replication by helioxanthin and its derivative," Antivir Chem Chemother. 2005;16(3):193-201.
The International Search Report and Written Opinion, issued on Apr. 14, 2014, in the corresponding PCT Patent Application No. PCT/EP2014/054763.

*Primary Examiner* — Suzanne M Noakes
*Assistant Examiner* — Stephen M. Chong

(57) ABSTRACT

The invention relates to the compounds of formula I and pharmaceutically acceptable salts and esters thereof, wherein $R^1$-$R^{11}$ are as defined in the description and claims. In addition, the present invention relates to methods of manufacturing and using the compounds of formula I as well as pharmaceutical compositions containing such compounds. The compounds of formula I are useful in differentiating stem cells into more mature or adult-like hepatocytes for use as drug screening platforms and in disease modeling applications.

8 Claims, 20 Drawing Sheets

Figure 1:
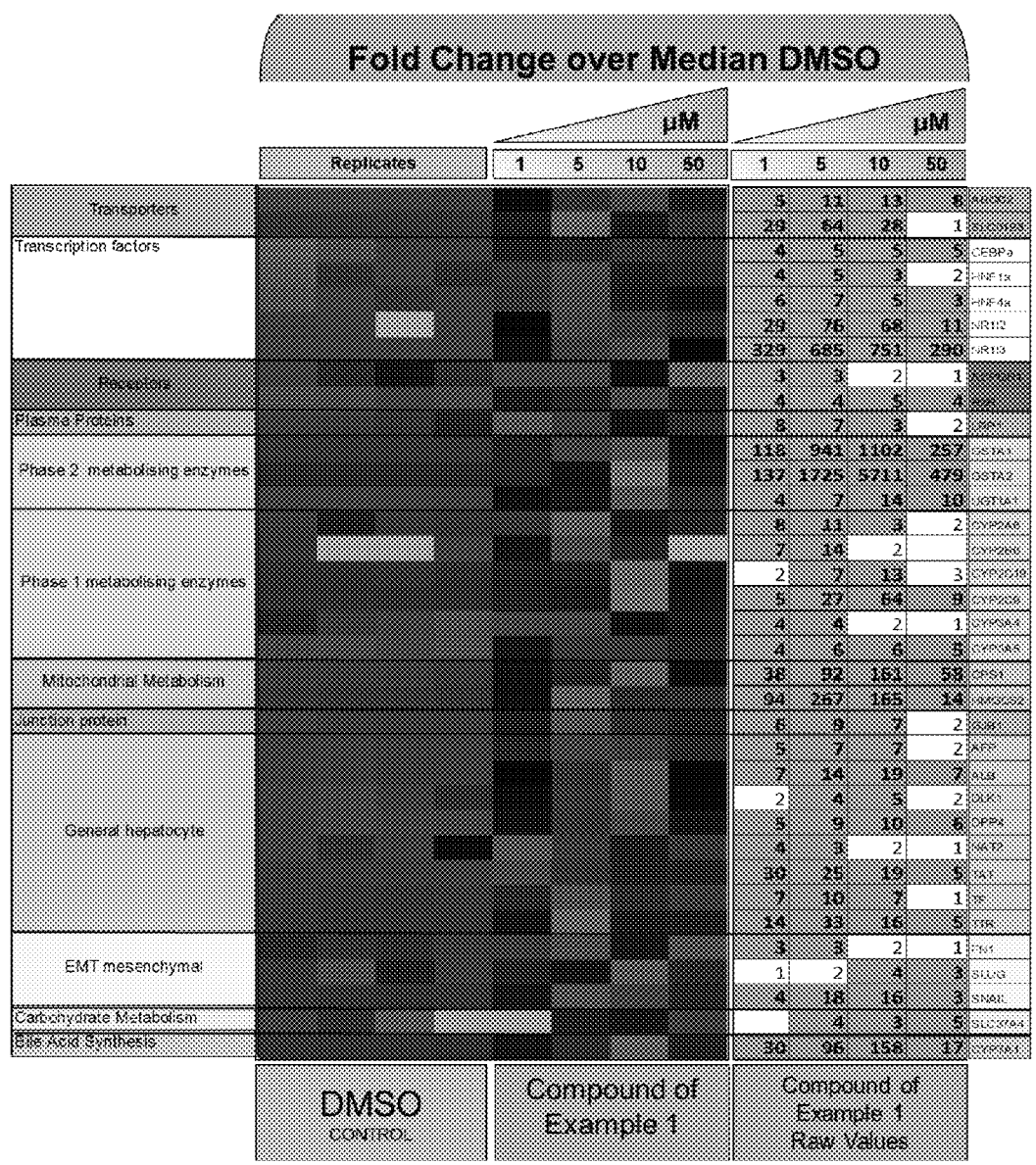

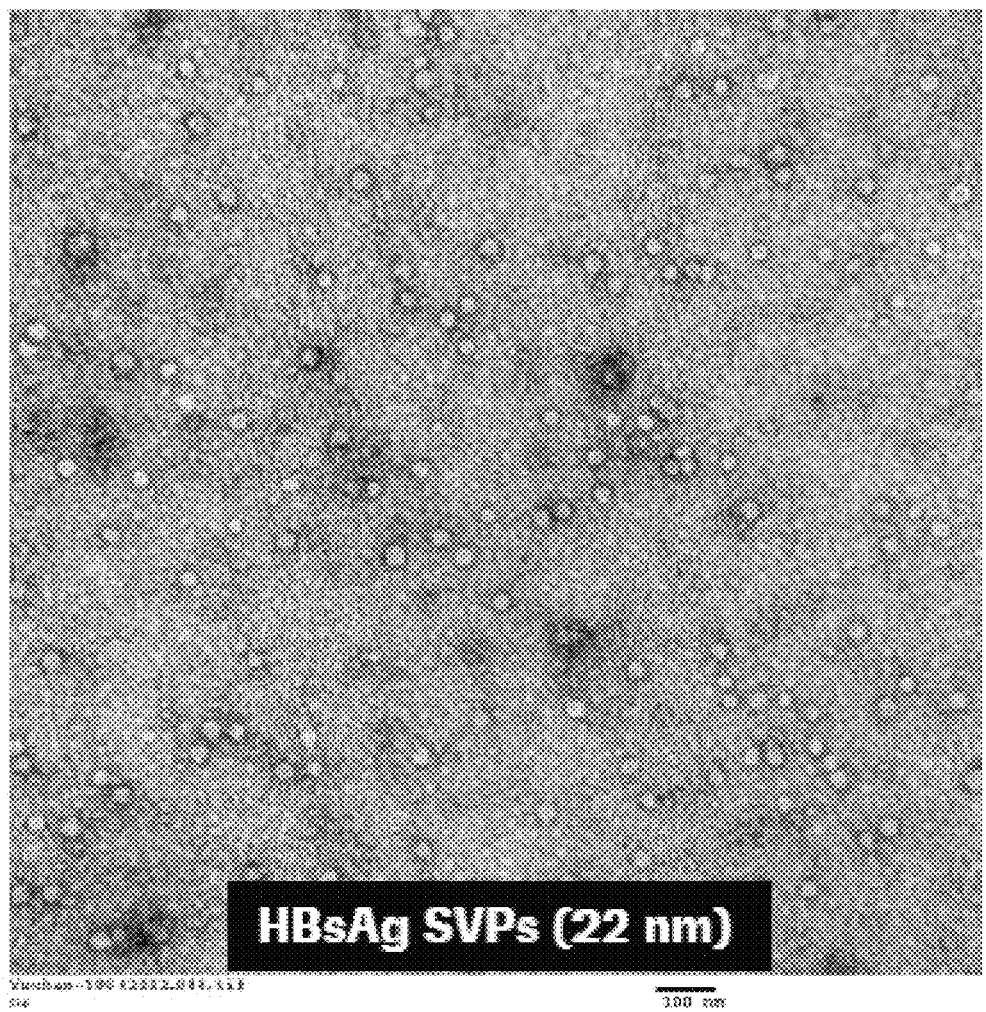
Fig. 15-I

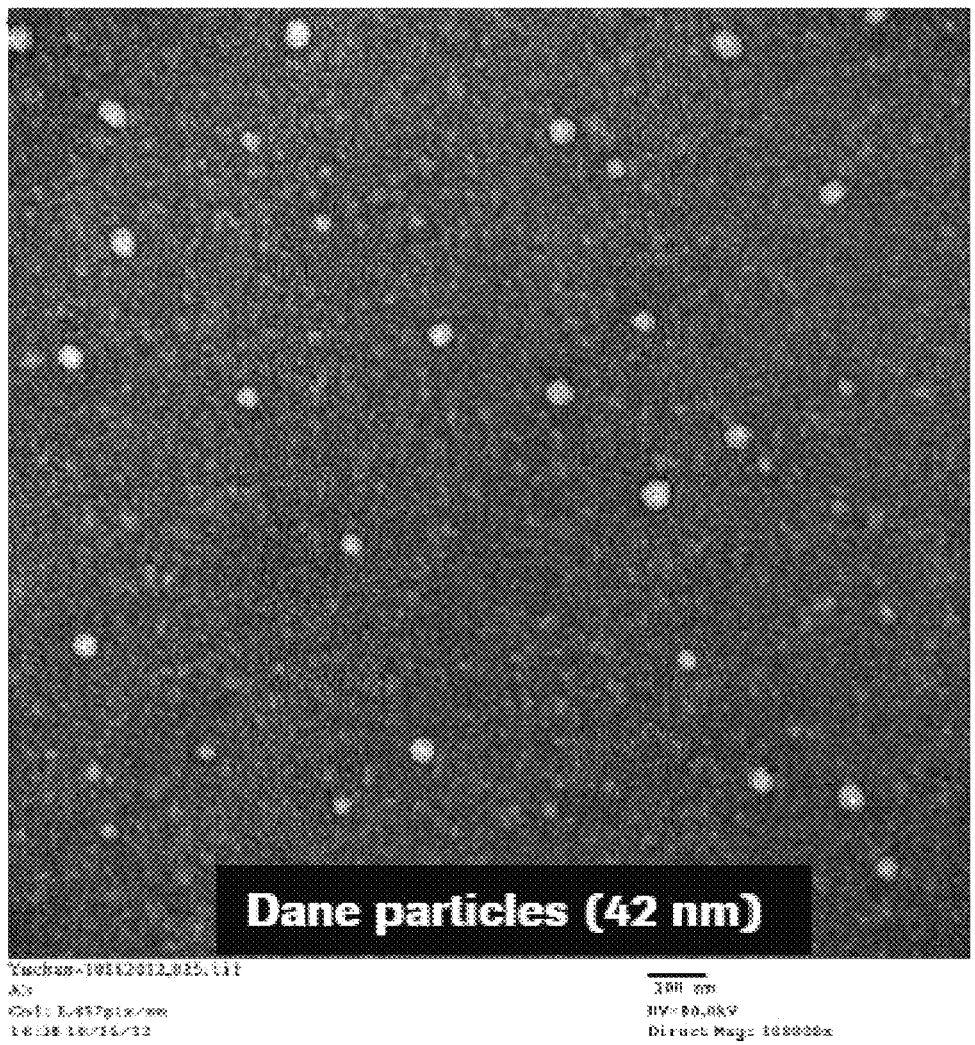
Fig. 15-II

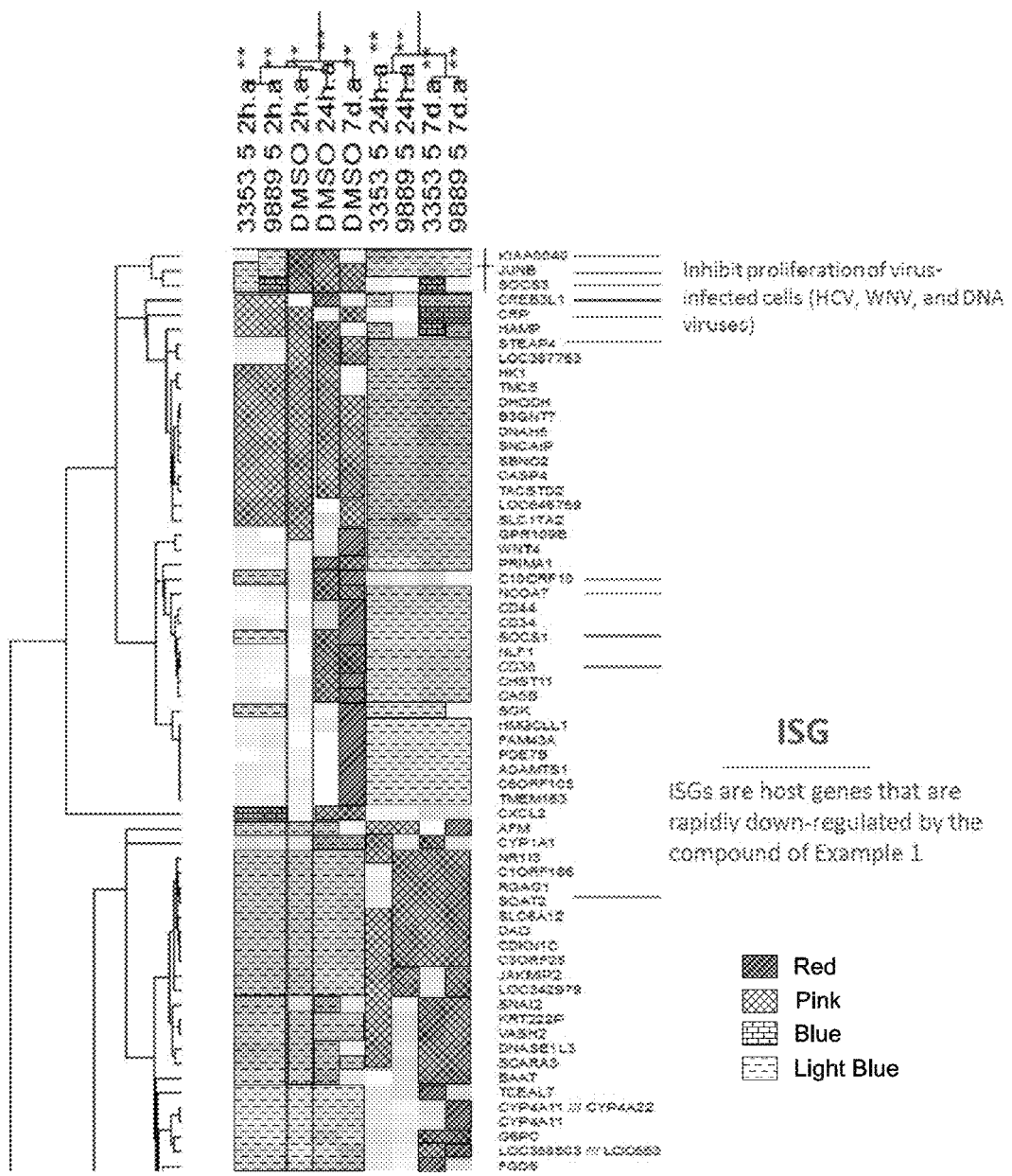
Fig. 16-I

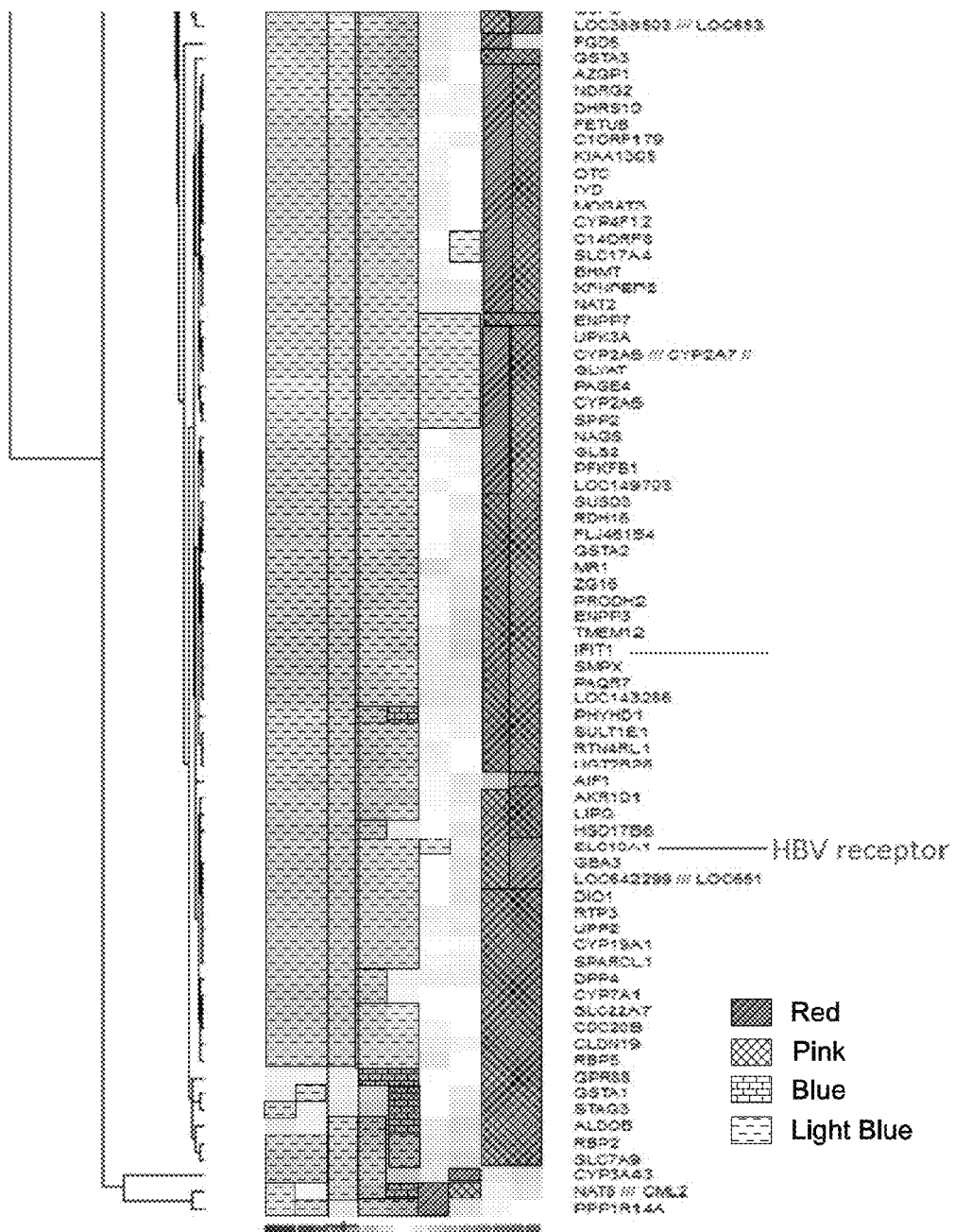
Fig. 16-II

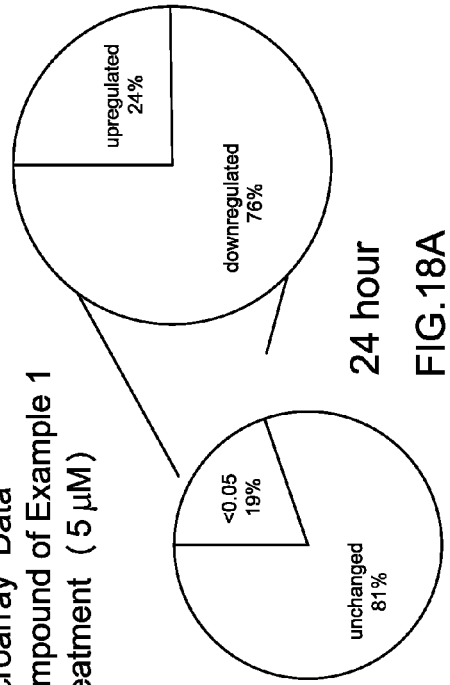

COMPOUNDS FOR IMPROVED STEM CELL DIFFERENTIATION INTO HEPATOCYTES

The present invention relates to compounds, their manufacture, and pharmaceutical compositions containing them for differentiating stem cells into more adult-like hepatocytes.

During drug discovery and development there is a tremendous need for robust in vitro methods for modeling liver function. Current methods employing primary human hepatocyte cultures have well-documented shortcomings, namely donor to donor variability and functional instability. Similarly, hepatoma cell lines exhibit functional insufficiency and suffer from confounding genetic abnormalities inherent in tumor cell lines.

Although pluripotent stem cell derived tissues hold promise to address the problem of donor to donor variability, thus far most reports examining human induced pluripotent stem cell (hiPSC)-derived hepatocytes indicate that they are more similar in certain functions to fetal tissues than adult, which could make their extrapolation to the adult in vivo situation difficult. Thus, there is a need for better methods of differentiating pluripotent stem cells into more mature or adult-like hepatocytes to generate more relevant models for drug discovery, efficacy, and safety testing.

Successful differentiation of hIPSC into adult-like hepatocytes will facilitate drug discovery efforts for treatment of chronic liver diseases such as hepatitis B virus (HBV) infection. Chronic HBV (CHB) infection is a huge unmet medical need affecting ~350 million people worldwide. Current treatments—nucleos(t)ide inhibitors and interferon (IFN)—are ineffective to clear the virus and are associated with viral resistance and/or adverse side effects. Based on the sequence variability of its viral genome, HBV is classified within 7 genotypes (genotype A-H; A-D being the major genotypes). The disease outcome of HBV infection are age- and genotype-dependent. Thus, most CHB infection results from vertical (mother-to-infant) transmission and/or infection during childhood. In contrast, ~90% of adults exposed to the virus were able to clear HBV infection within 6 months. In addition, various clinical data have shown that viral genotypes influence HBV disease progression and response to IFN treatment. HBV is also known to evade host immune responses by various mechanisms including down-regulation of interferon-stimulated genes (ISGs). A better understanding of the complex interplay between HBV and host innate immunity may lead to new host/viral targets for treatment of CHB infection. However, efforts to discover novel, more efficacious antivirals for HBV have been hampered by the lack of physiological and robust in vitro systems. Current hepatoma-based systems, used both as producer- and target-cells, are neither robust nor capture the genotype diversity of HBV. Thus, new in vitro systems that are more physiologically relevant and support robust infection of all major HBV genotypes, preferably from clinical isolates, will be highly desirable. Such systems will not only be beneficial as drug screening platforms, but also for HBV disease modeling including assessment of genotype-dependent of interferon response.

Thus, there is a need for improved differentiation of stem cell-derived hepatocytes into more mature hepatocytes to support robust infection of patient-derived HBV from various genotypes for use as drug screening platforms and disease modeling.

The invention is concerned with the compounds of formula I:

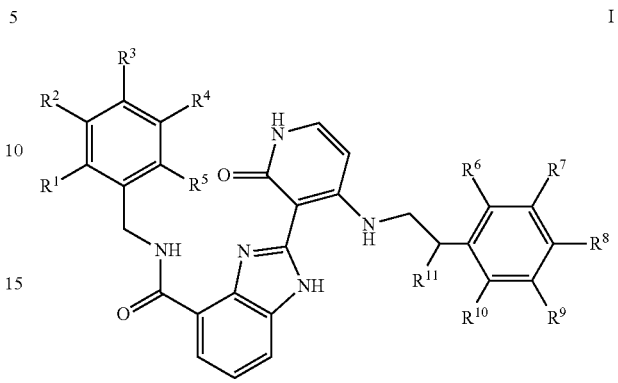

and pharmaceutically acceptable salts and esters thereof, wherein $R^1$-$R^{11}$ are as defined hereinafter. In addition, the present invention relates to methods of manufacturing and using the compounds of formula I as well as pharmaceutical compositions containing such compounds. The compounds of formula I are useful in differentiating stem cells into more mature or adult-like hepatocytes for use as drug screening platforms and in disease modeling platforms.

FIG. 1 provides a heat map showing the global increased expression of genes spanning hepatocyte function at multiple doses using the compound of example 1. Biology heat maps are typically used in molecular biology to represent the level of expression of many genes across a number of comparable samples (e.g. cells in different states, samples from different patients) as they are obtained from cDNA samples. 'Green' indicates low expression whereas 'Red' indicates high expression in FIG. 1. The graphical representation is relative across each row of data creating a gradient from lowest expression (green) to median (black) to highest expression (red).

Figure 2:
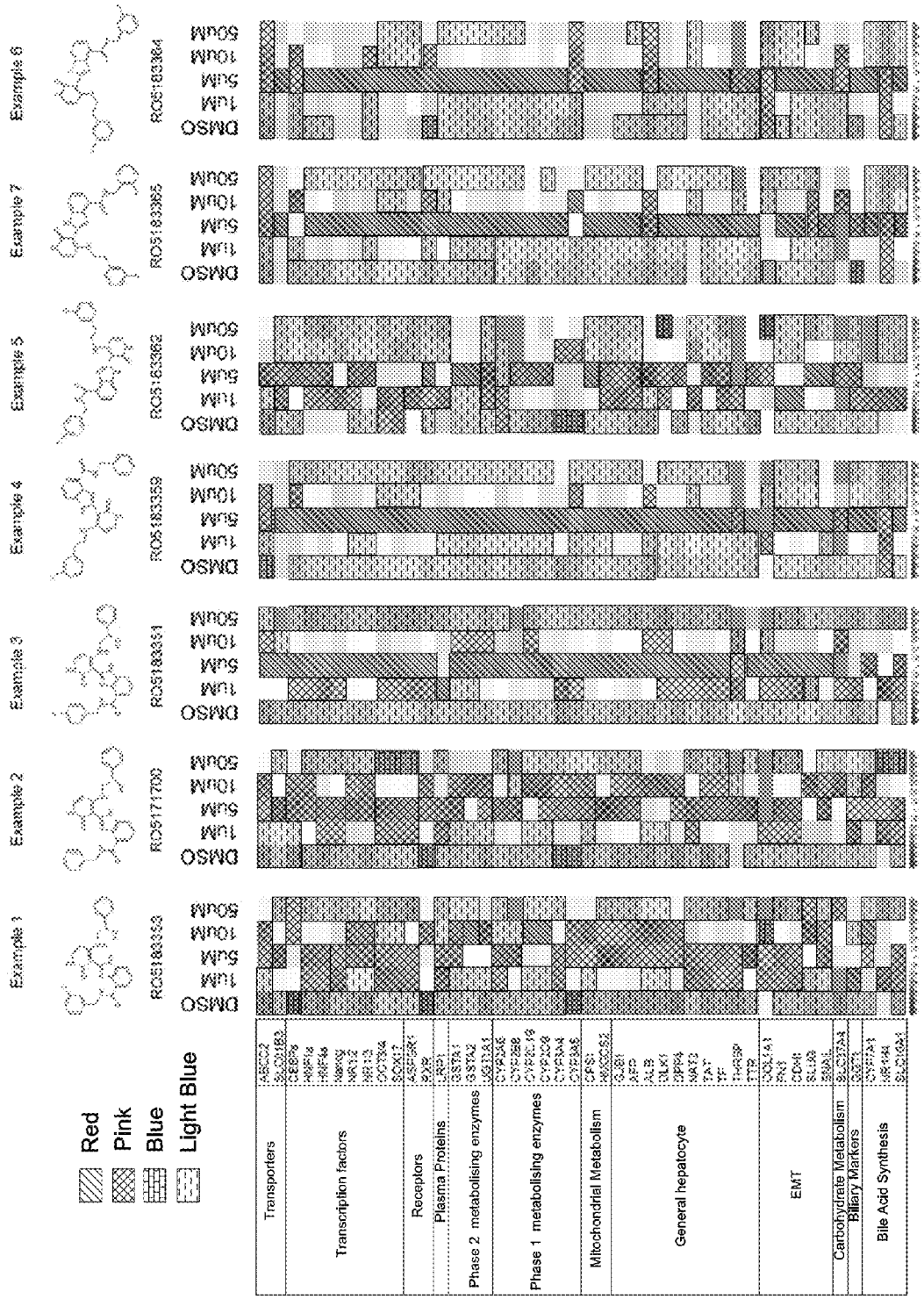

FIG. 2 shows the increased expression of genes spanning hepatocyte function in induced pluripotent stem cell derived hepatocytes based on gene expression of a panel of maturation-associated genes after treatment with the compounds of examples 1-7.

Figure 3:
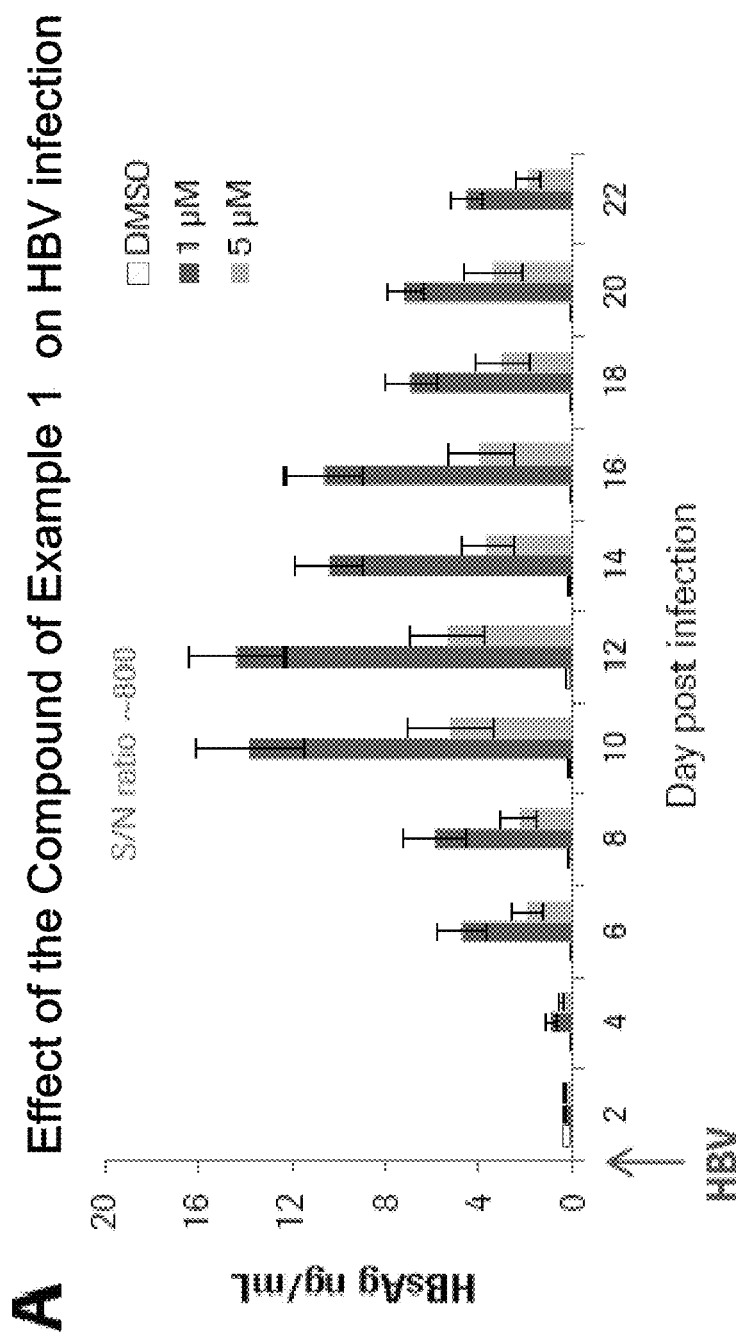
Figure 4:
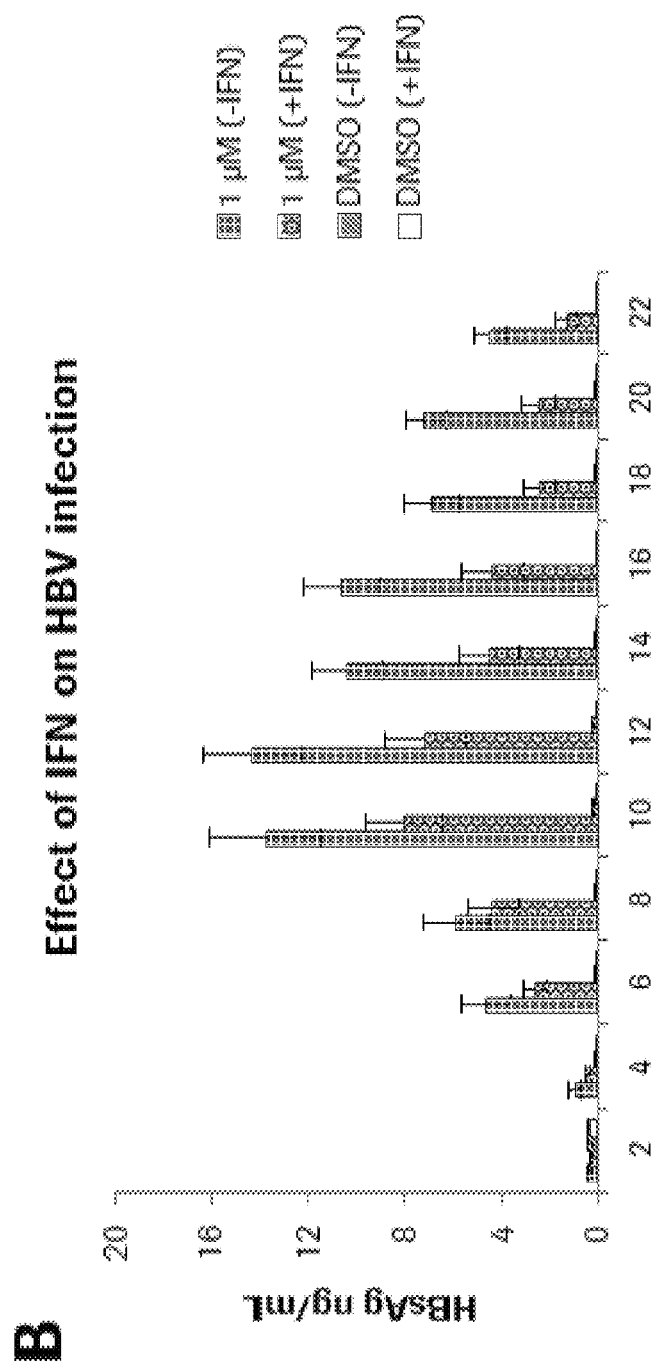
Figure 5:
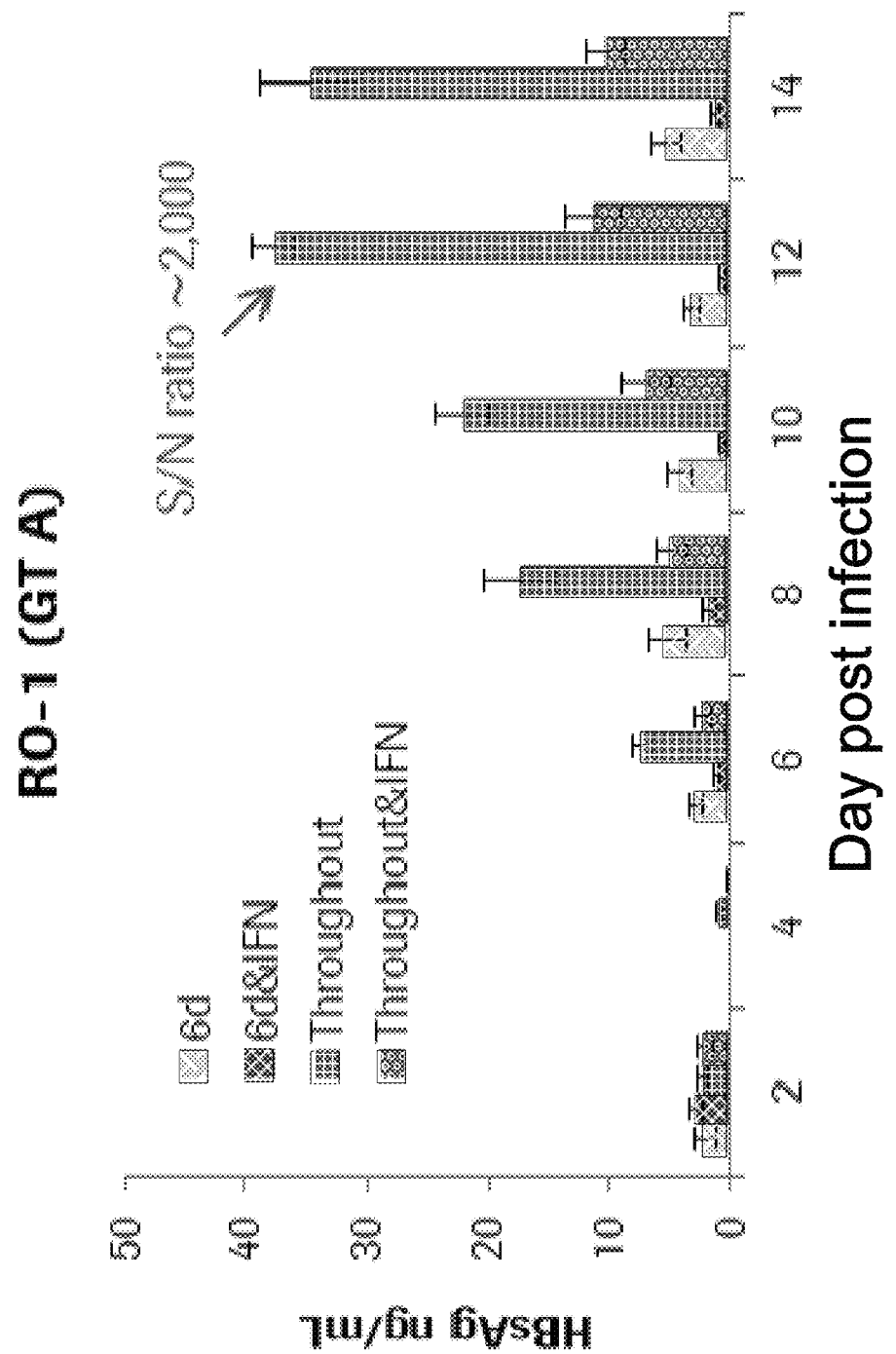
Figure 6:
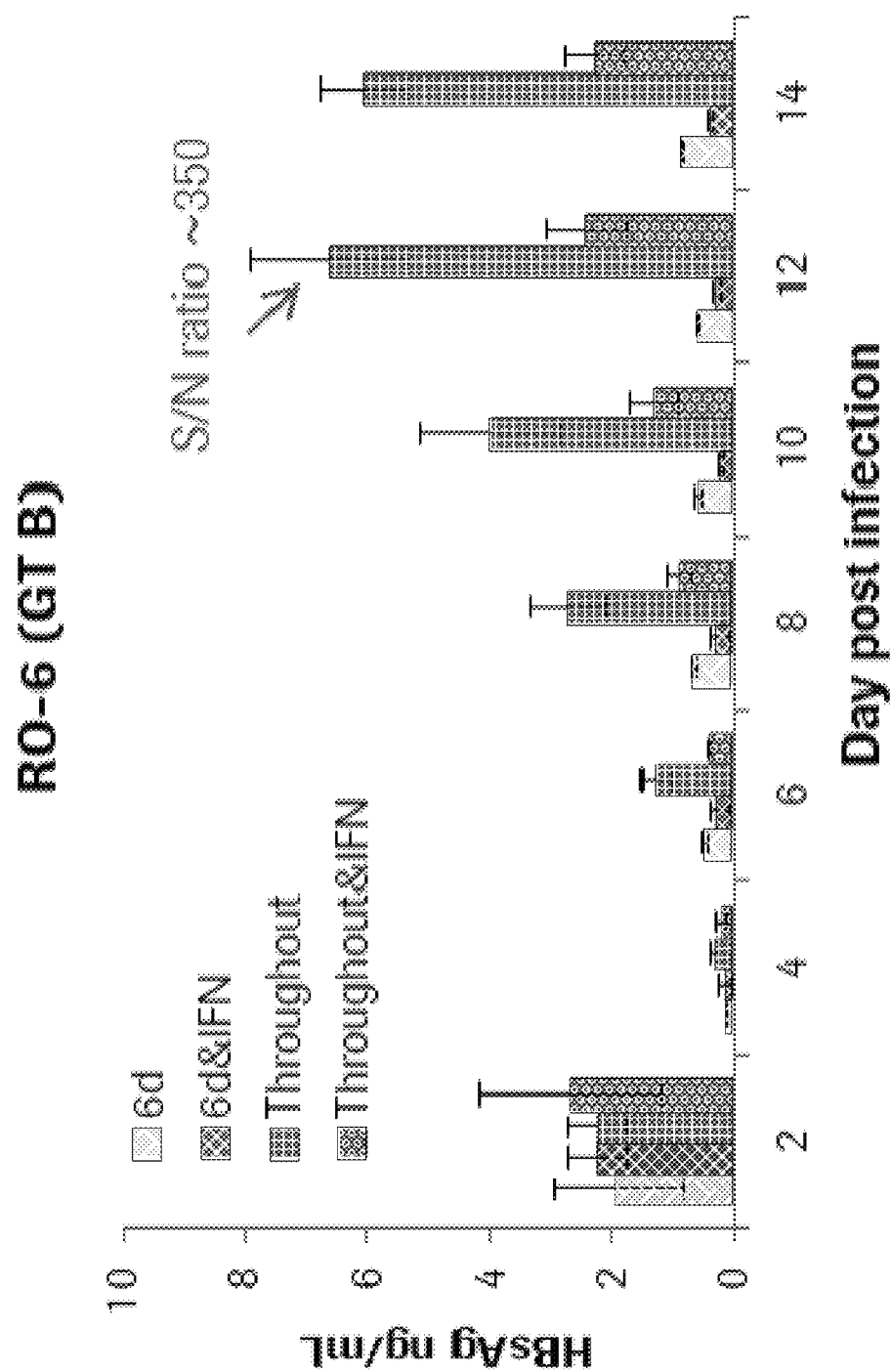
Figure 7:
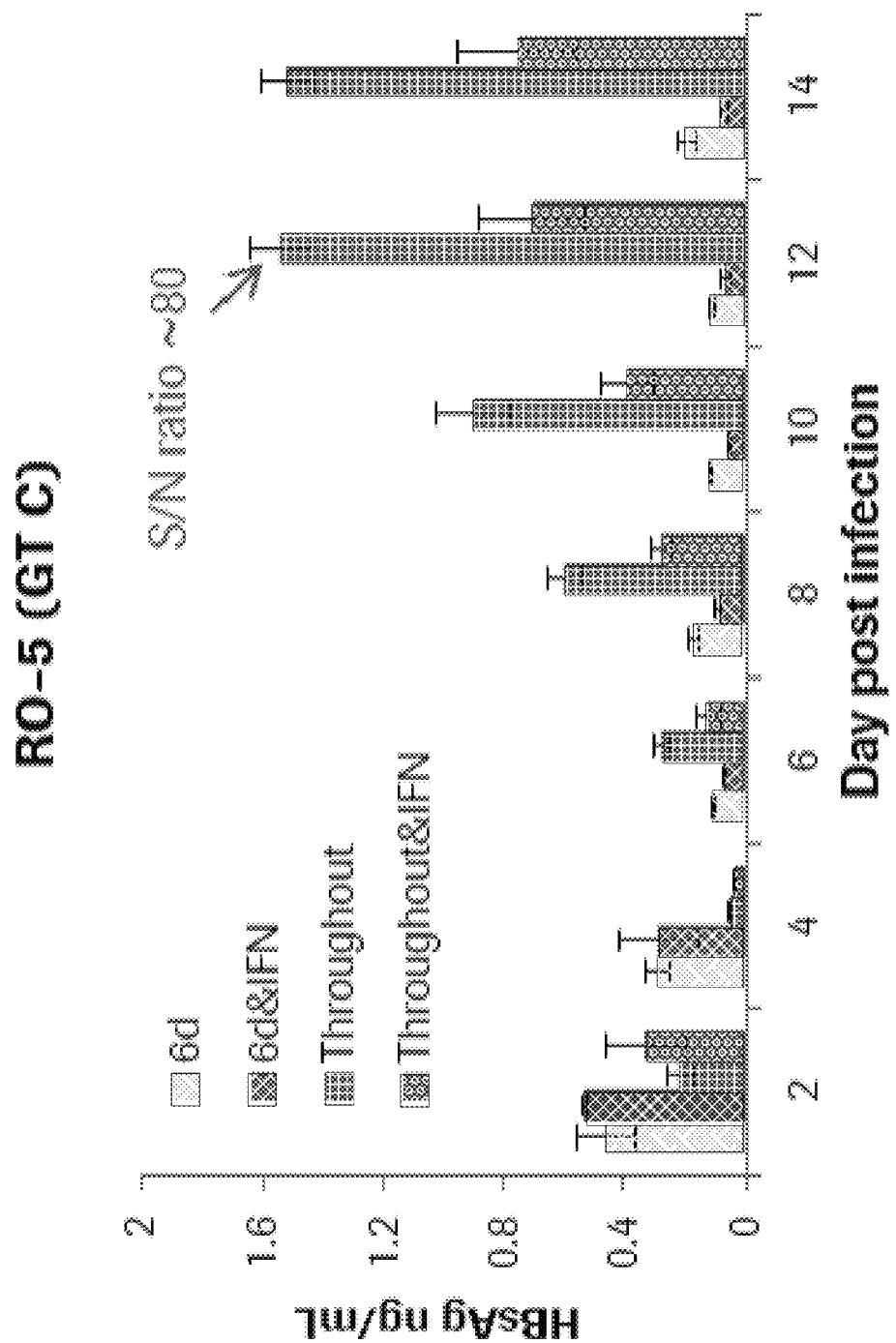

FIGS. 3 and 4 show a robust HBV infection in iCell hepatocytes. FIG. 3 is a bar graph showing that treatment of induced pluripotent stem cell derived hepatocytes with the compound of example 1 led to cell susceptibility to HBV infection that occurred in a dose-dependent manner. FIG. 4 is a bar graph showing that viral infection is inhibited by interferon (100 IU/ml).

FIGS. 4, 5, 6 and 7 show the pan-genotypic HBV infection in iCell hepatocytes and are a series of bar graphs reflecting that induced pluripotent stem cell derived hepatocytes treated with the compound of example 1 are able to support robust infection of all four major HBV genotypes. Continuous presence of the compound of example 1 is required to maintain robust viral infection. Cells either were pre-treated with the compound of example 1 for 6 d before HBV infection (6 d), or pre-treated for 6 days and during infection (throughout). Interferon (IFN) is used to show the specificity of HBV infection.

Figure 8:
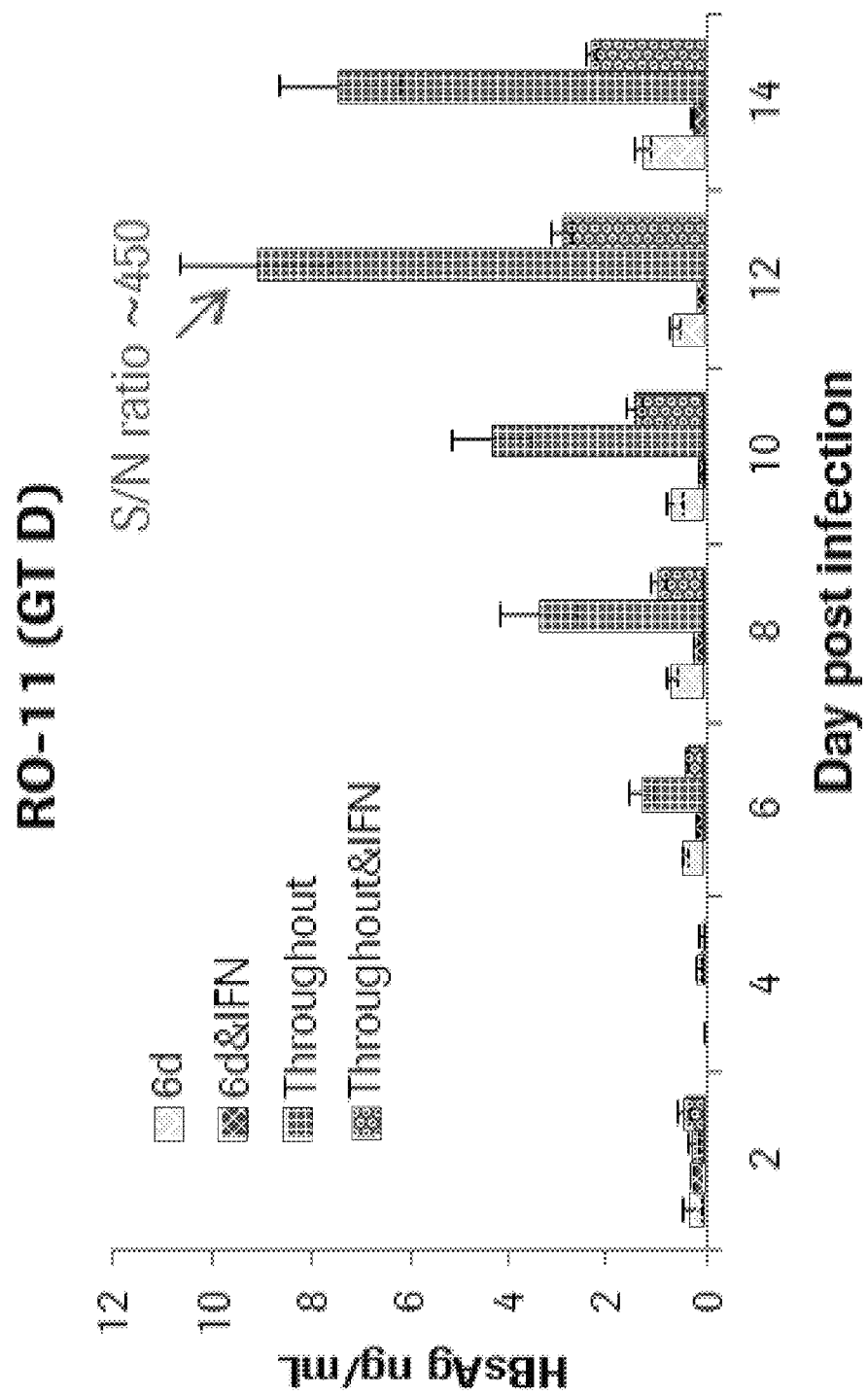
Figure 9:
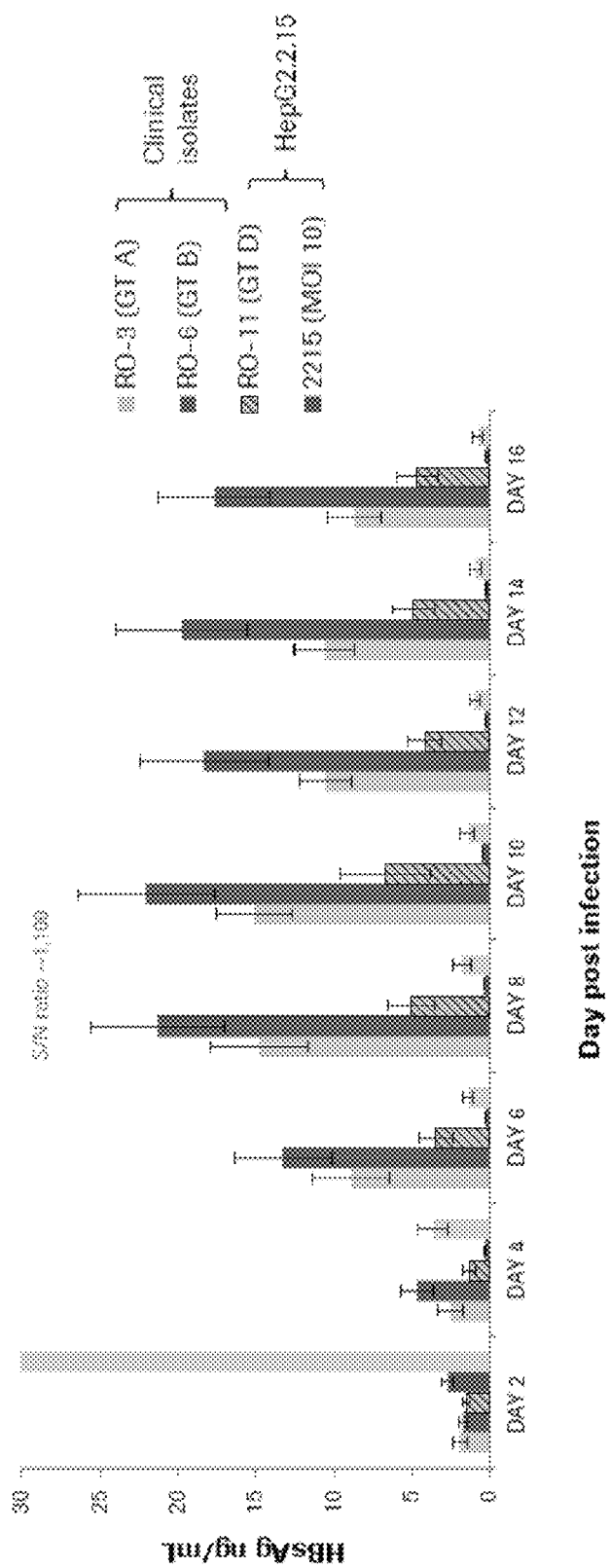
Figure 10:
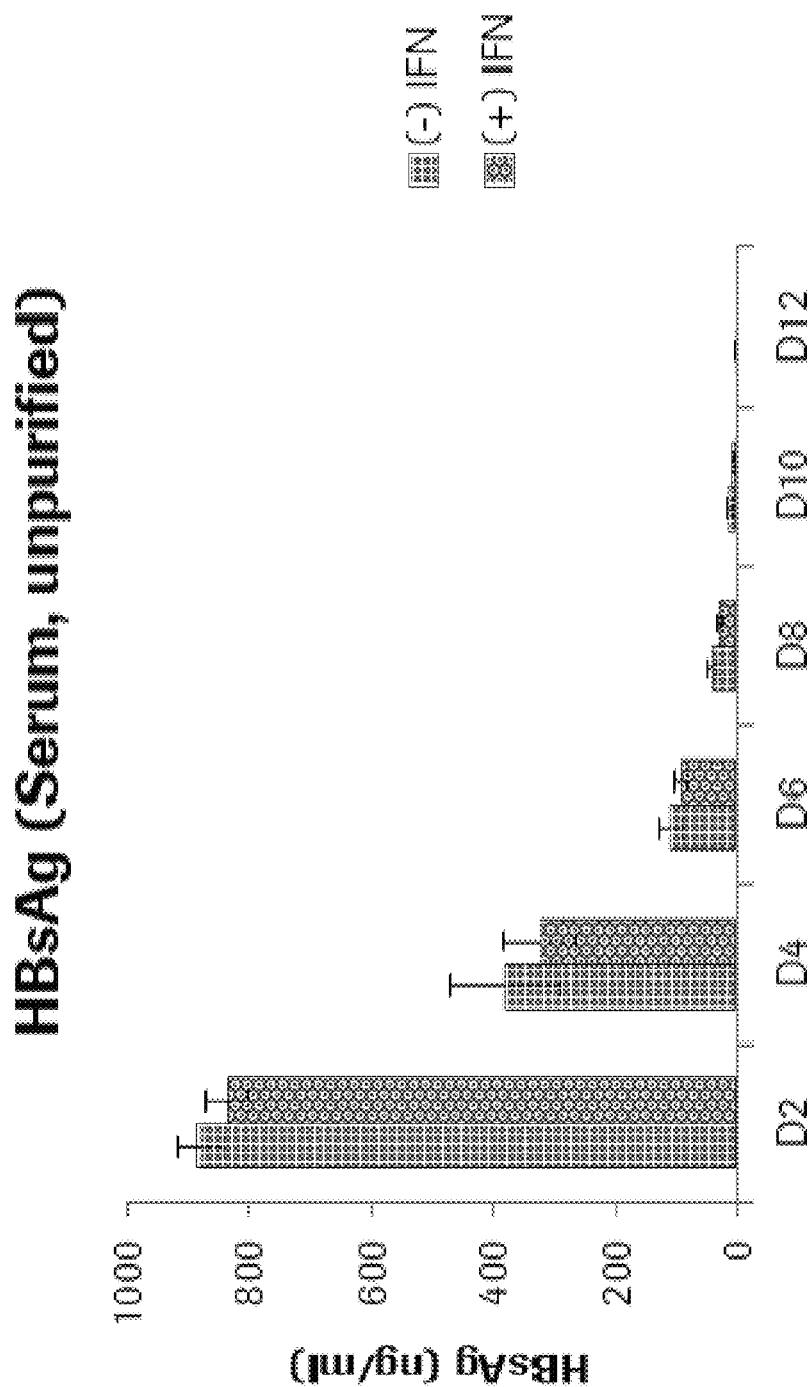

FIG. 8 is a bar graph showing that induced pluripotent stem cell derived hepatocytes treated with the compound of example 1 support infection of HBV isolated from patient sera (clinical isolates), and not from cell culture-derived virus (HepG2.2.15). iCell hepatocytes treated with the compound of example 1 support infection of patient-derived, but not cell culture-derived, HBV.

FIGS. 9, 10, 11 and 12 relate to HBV infectivity: serum vs. purified virus and are a series of bar graphs showing that removal of excess of HBsAg subviral particles (SVPs) present in serum is a prerequisite to achieve robust HBV infection in induced pluripotent stem cell derived hepatocytes treated with the compound of example 1. Cells were pre-treated with the compound of example 1 for 6 d before HBV infection (6 d).

Figure 13:
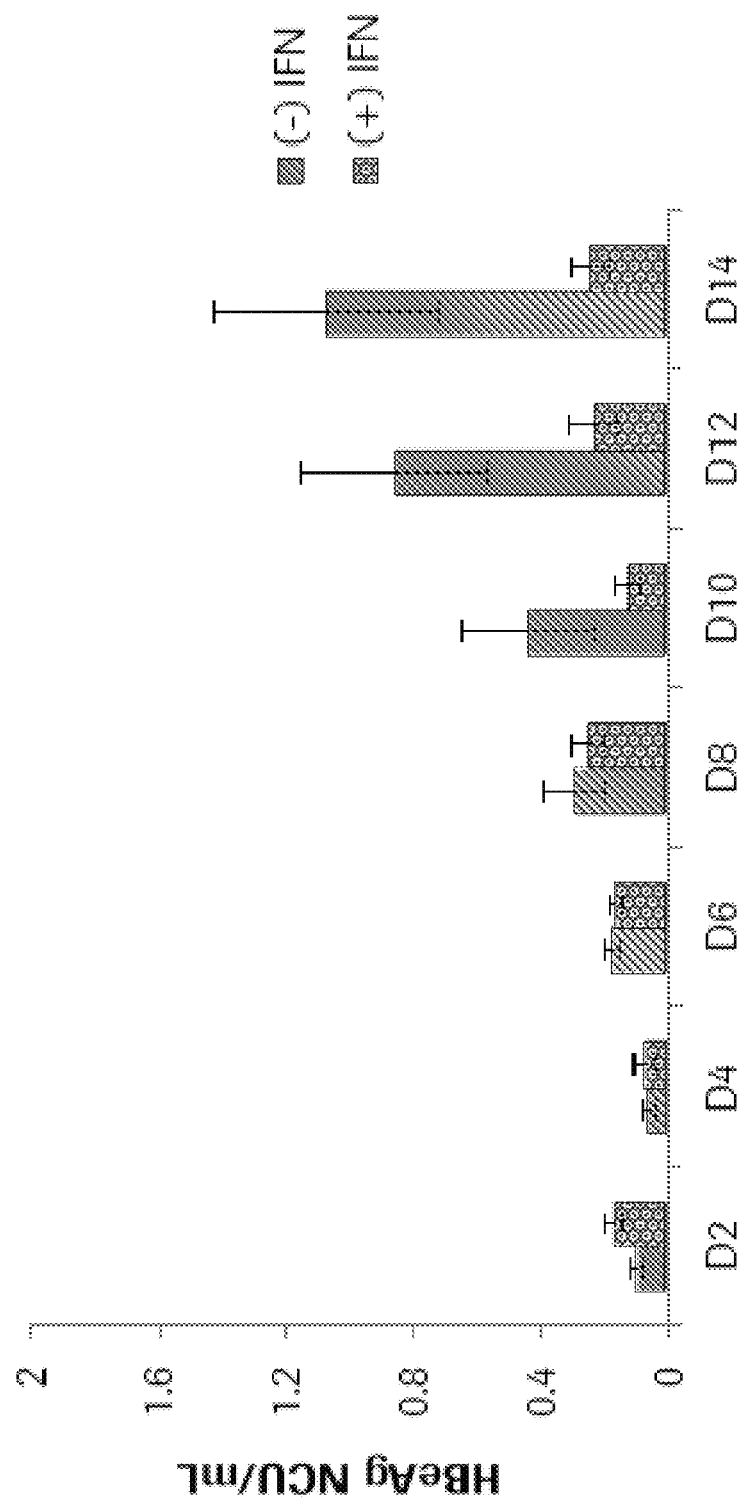
Figure 14:
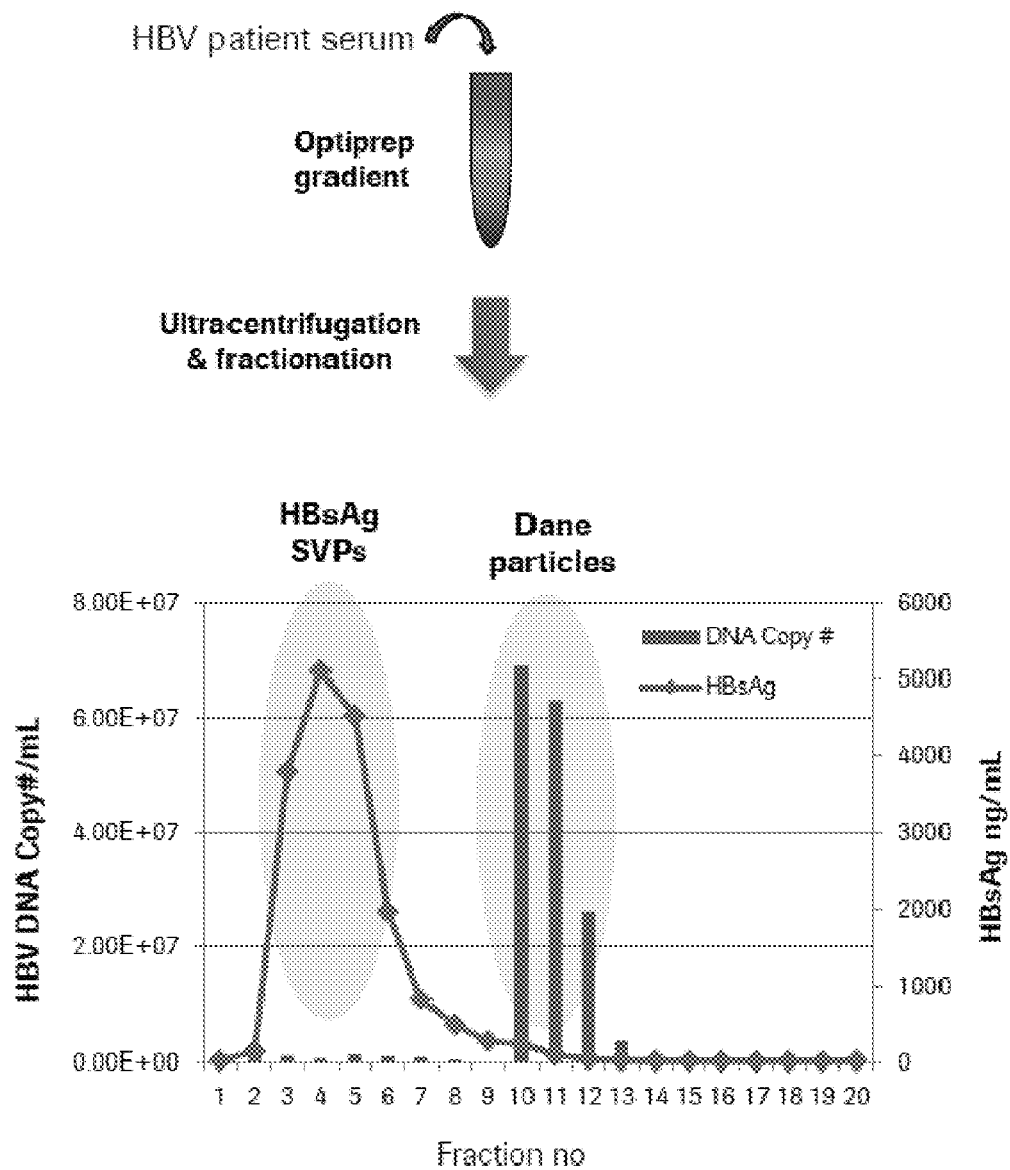

FIGS. 13 and 14 relate to the purification of HBV virus particles from excess HBsAg subviral particles (SVPs) and show that purified virus (Dane particles) were separated from HBsAg SVPs by Optiprep gradient ultracentrifugation. Viral markers (HBsAg and HBV DNA) and electron microscopy analysis were used to confirm that virus purification was successful.

Figure 11:
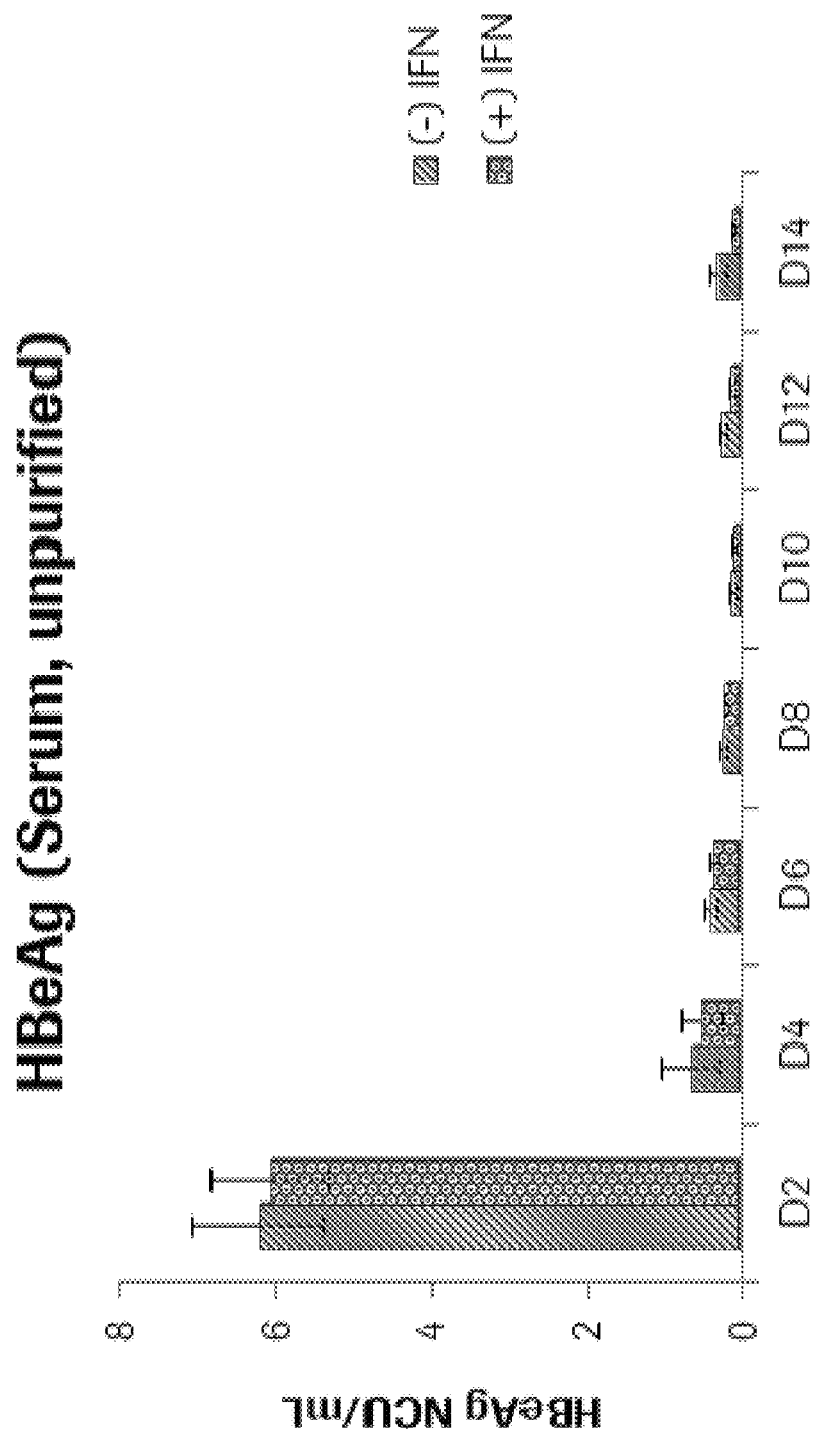
Figure 12:
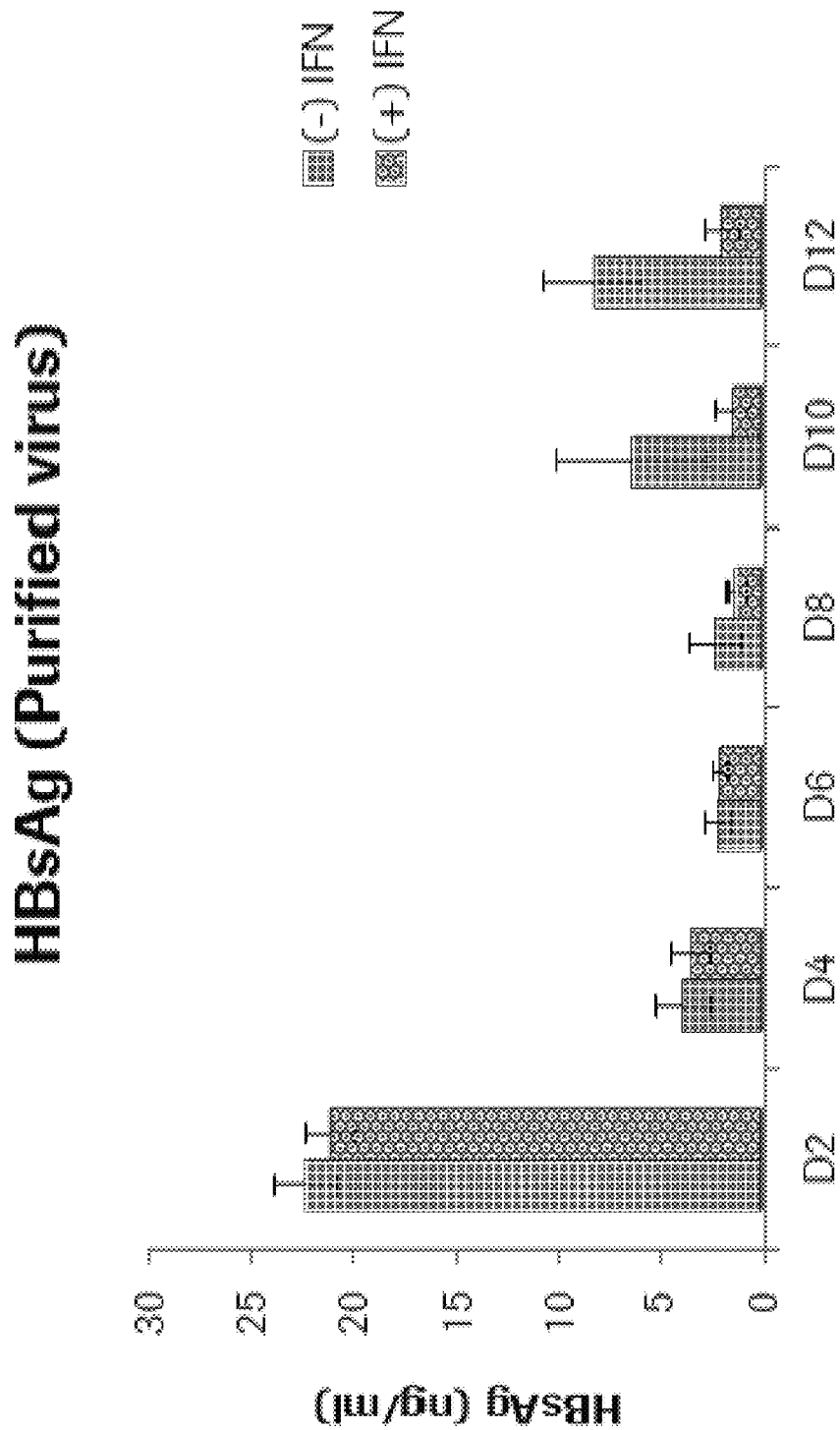

FIG. 15-I is a microarray analysis (heat map-light photo) and FIG. 15-11 (dark photo) of induced pluripotent stem cell derived hepatocytes treated with the compound of example 1. Genes that were up- and down-regulated >2-fold (2 hr), >3-fold (24 hr), or >6-fold (7 day) post treatment are shown. The compound of example 1 down-regulated interferon-stimulated genes (ISGs) as early as 2 hr. Two genes (non-ISGs) that may also play roles in iCell hepatocyte susceptibility to HBV infection are shown: CREB3L1 (down-regulated as early as 2 hr post treatment) is shown to inhibit proliferation of infected cells by other viruses (HCV, WNV, and DNA viruses), and SLC10A1 (up-regulated at 7 day post-treatment) has been reported as an HBV receptor.

Figure 17:
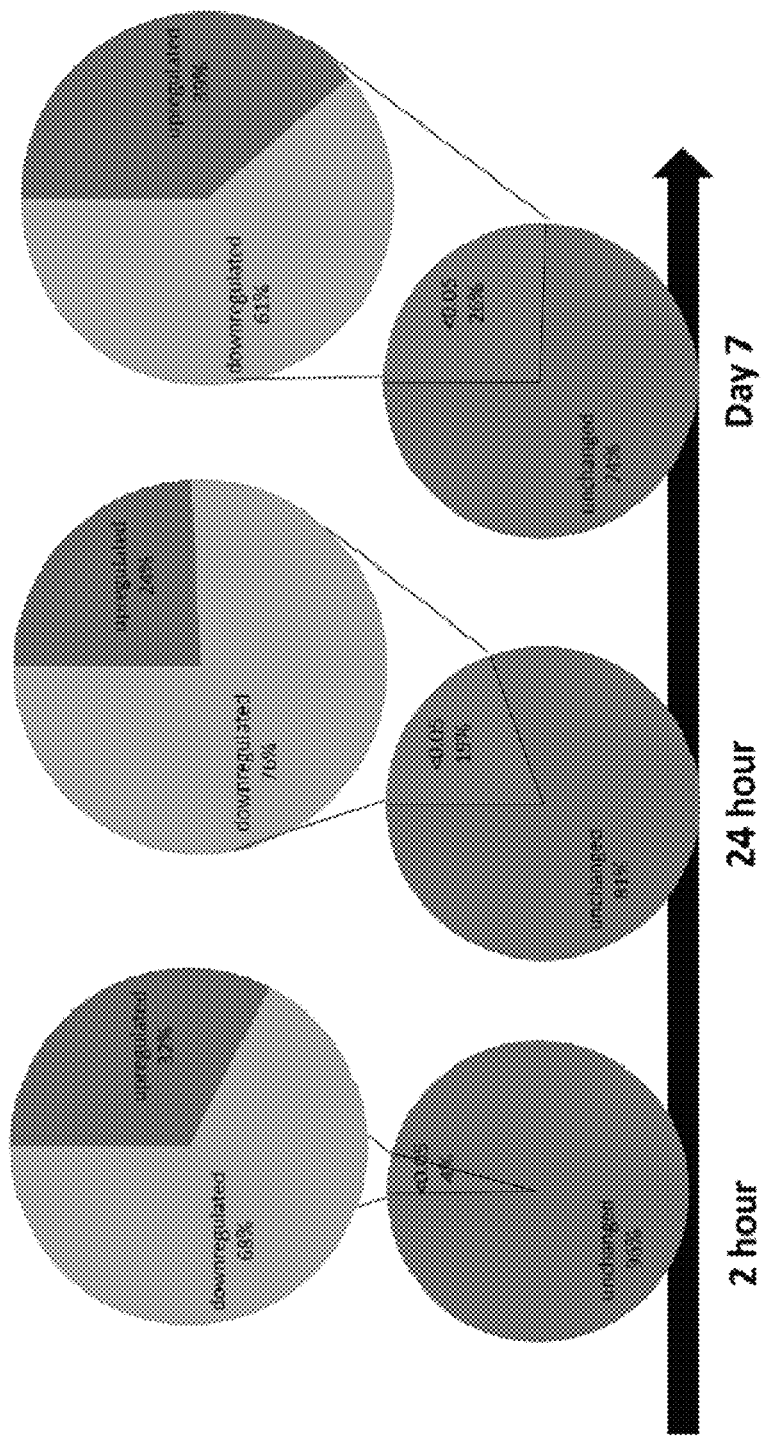

FIGS. 16-I and 16-II relate to the effect of the compound of example 1 on interferon-stimulated genes (ISGs) and provides pie charts (FIG. 17) showing the kinetic effect of the compound of example 1 on ISGs expression in induced pluripotent stem cell derived hepatocytes. A list of 975 interferon-stimulated genes (ISGs) are based on known ISGs in the public data database (see Table 1). 16-I and 16-II continue with each other.

FIGS. 18A-D relate to the effect of compound of example 1 on ISG expression (975 genes) and provides pie charts showing examples of ISGs modulated by the compound of example 1 at 24 hr and 7 day post compound treatment. The list of 975 interferon-stimulated genes (ISGs) are based on known ISGs in the public data database (see Table 1).

Table 1 shows the kinetic effect of the compound of example 1 on ISGs at 2 hr, 24 hr, and 7 day post treatment (p-value <0.05).

TABLE 1

| 2 HOUR | | | 24 HOUR | | |
|---|---|---|---|---|---|
| Gene_Symbol | Raw Est Fold Change | Un-adjusted p-value | Gene_Symbol | Raw Est Fold Change | Un-adjusted p-value |
| BUB1 | −20.72 | 0.0012 | STEAP4 | −65.16 | 0.0000 |
| RHOH | −14.71 | 0.0068 | BUB1 | −33.18 | 0.0010 |
| CD80 | −13.65 | 0.0032 | SPTLC2 | −10.08 | 0.0160 |
| SOCS3 | −9.95 | 0.0002 | CD38 | −10.02 | 0.0120 |
| JUNB | −6.01 | 0.0009 | SOCS1 | −9.88 | 0.0002 |
| JAK1 | −5.55 | 0.0044 | THBD | −9.02 | 0.0349 |
| HLA-C | −4.87 | 0.0002 | NFE2 | −8.28 | 0.0164 |
| ABCA9 | −4.37 | 0.0101 | FFAR2 | −7.50 | 0.0024 |
| SOCS1 | −4.13 | 0.0086 | C4orf32 | −7.20 | 0.0003 |
| C10orf10 | −3.72 | 0.0119 | IFI16 | −6.86 | 0.0024 |
| MPO | −3.18 | 0.0426 | AXL | −6.82 | 0.0051 |
| EPAS1 | −2.61 | 0.0016 | MT1X | −6.73 | 0.0031 |

TABLE 1-continued

| KAL1 | −2.61 | 0.0382 | ICAM1 | −6.60 | 0.0072 |
|---|---|---|---|---|---|
| ETV7 | −2.54 | 0.0380 | EMP1 | −5.94 | 0.0498 |
| PCP4 | −2.44 | 0.0402 | GALNT2 | −5.18 | 0.0036 |
| TXNIP | −2.04 | 0.0210 | CASP4 | −5.09 | 0.0012 |
| PHF11 | −1.80 | 0.0134 | KIAA0040 | −5.04 | 0.0004 |
| FGF2 | −1.76 | 0.0094 | JUNB | −4.94 | 0.0005 |
| AKT3 | −1.76 | 0.0495 | RBL1 | −4.92 | 0.0473 |
| EFNB2 | −1.63 | 0.0194 | IL6 | −4.57 | 0.0448 |
| BCL3 | −1.44 | 0.0449 | TMEM67 | −4.34 | 0.0358 |
| CEBPD | −1.29 | 0.0413 | IL8 | −4.32 | 0.0043 |
| GTPBP2 | −1.29 | 0.0099 | ETV7 | −3.88 | 0.0149 |
| PIM3 | −1.19 | 0.0328 | IRF7 | −3.86 | 0.0161 |
| ISGF3G | −1.17 | 0.0152 | MAP3K8 | −3.81 | 0.0009 |
| EHHADH | −1.16 | 0.0431 | HEG1 | −3.64 | 0.0194 |
| PCMT1 | −1.10 | 0.0407 | MYT1 | −3.59 | 0.0432 |
| PI4K2B | −1.08 | 0.0291 | SOCS3 | −3.51 | 0.0069 |
| CSNK1D | 1.10 | 0.0309 | MT1M | −3.35 | 0.0130 |
| KPNB1 | 1.14 | 0.0136 | PLSCR1 | −3.34 | 0.0013 |
| PXK | 1.17 | 0.0366 | AMPH | −3.29 | 0.0047 |
| DRAP1 | 1.17 | 0.0269 | CREB3L3 | −3.22 | 0.0206 |
| GOLGA3 | 1.45 | 0.0117 | BCL3 | −3.11 | 0.0022 |
| SCARB2 | 1.50 | 0.0460 | IFITM1 | −3.11 | 0.0438 |
| PHF15 | 1.74 | 0.0284 | GBP4 | −3.07 | 0.0095 |
| ASNS | 1.80 | 0.0131 | ATF3 | −3.06 | 0.0017 |
| AES | 2.07 | 0.0496 | CASP5 | −3.00 | 0.0268 |
| DDIT4 | 2.67 | 0.0061 | EGR1 | −2.86 | 0.0009 |
| ADAM19 | 2.77 | 0.0284 | EPAS1 | −2.84 | 0.0010 |
| MAX | 3.74 | 0.0081 | NPAS2 | −2.77 | 0.0069 |
| CD300LF | 5.42 | 0.0379 | C10orf10 | −2.71 | 0.0047 |
| | | | CYP1B1 | −2.71 | 0.0070 |
| | | | IER3 | −2.60 | 0.0003 |
| | | | CEBPD | −2.58 | 0.0022 |
| | | | PIM3 | −2.56 | 0.0014 |
| | | | GK | −2.50 | 0.0089 |
| | | | IFNGR1 | −2.46 | 0.0016 |
| | | | PNRC1 | −2.42 | 0.0051 |
| | | | CSDA | −2.38 | 0.0154 |
| | | | TEAD4 | −2.33 | 0.0021 |
| | | | RAB27A | −2.33 | 0.0001 |
| | | | MTHFD2L | −2.20 | 0.0231 |
| | | | LRP4 | −2.17 | 0.0255 |
| | | | STAT1 | −2.14 | 0.0142 |
| | | | HLA-DPB1 | −2.11 | 0.0189 |
| | | | LRG1 | −2.10 | 0.0426 |
| | | | HLA-DPA1 | −2.10 | 0.0476 |
| | | | MAFF | −2.09 | 0.0007 |
| | | | TMEM49 | −2.07 | 0.0189 |
| | | | MSR1 | −2.06 | 0.0383 |
| | | | IGHM | −2.00 | 0.0224 |
| | | | SQLE | −1.98 | 0.0067 |
| | | | USP12 | −1.96 | 0.0259 |
| | | | ITGA2 | −1.94 | 0.0317 |
| | | | IFITM2 | −1.90 | 0.0037 |
| | | | FKBP1B | −1.90 | 0.0464 |
| | | | FUT4 | −1.89 | 0.0458 |
| | | | HK2 | −1.88 | 0.0001 |
| | | | B4GALT5 | −1.87 | 0.0040 |
| | | | SERPINB9 | −1.86 | 0.0057 |
| | | | PSMB9 | −1.86 | 0.0115 |
| | | | PDGFRL | −1.86 | 0.0367 |
| | | | PCTK2 | −1.85 | 0.0318 |
| | | | ZNF295 | −1.84 | 0.0001 |
| | | | GBP2 | −1.83 | 0.0027 |
| | | | CCND3 | −1.81 | 0.0045 |
| | | | ADM | −1.81 | 0.0034 |
| | | | IMPA2 | −1.80 | 0.0047 |
| | | | MLKL | −1.78 | 0.0219 |
| | | | FLT1 | −1.75 | 0.0454 |
| | | | ETS2 | −1.73 | 0.0077 |
| | | | ARHGDIB | −1.72 | 0.0228 |
| | | | BST2 | −1.70 | 0.0187 |
| | | | ISG20 | −1.70 | 0.0013 |
| | | | IQGAP1 | −1.70 | 0.0260 |
| | | | FNDC3B | −1.67 | 0.0005 |
| | | | SFTPC | −1.66 | 0.0118 |
| | | | CYBA | −1.64 | 0.0030 |
| | | | C1S | −1.62 | 0.0023 |
| | | | TAP1 | −1.60 | 0.0330 |
| | | | FNDC4 | −1.59 | 0.0020 |
| | | | SLC15A2 | −1.58 | 0.0023 |

TABLE 1-continued

| Gene_Symbol | Fold Change | p-value |
|---|---|---|
| SAT | −1.57 | 0.0047 |
| IFI27 | −1.56 | 0.0314 |
| DDX17 | −1.56 | 0.0039 |
| TAP2 | −1.54 | 0.0062 |
| FAM125B | −1.54 | 0.0143 |
| SLC25A28 | −1.54 | 0.0079 |
| CD47 | −1.52 | 0.0133 |
| FUBP1 | −1.50 | 0.0293 |
| PPP1R3D | −1.49 | 0.0041 |
| PDK1 | −1.48 | 0.0461 |
| NUB1 | −1.47 | 0.0435 |
| HIF1A | −1.47 | 0.0019 |
| EFNB2 | −1.46 | 0.0052 |
| SQRDL | −1.45 | 0.0377 |
| THBS1 | −1.44 | 0.0100 |
| ABHD5 | −1.43 | 0.0363 |
| UBE2S | −1.40 | 0.0442 |
| N4BP1 | −1.40 | 0.0219 |
| SFPQ | −1.39 | 0.0284 |
| FKBP5 | −1.39 | 0.0035 |
| TFPI | −1.38 | 0.0032 |
| NFKBIA | −1.38 | 0.0066 |
| RBMS1 | −1.38 | 0.0010 |
| ISGF3G | −1.37 | 0.0466 |
| ETV6 | −1.37 | 0.0216 |
| TXNIP | −1.37 | 0.0419 |
| IFITM3 | −1.36 | 0.0154 |
| TMEM2 | −1.35 | 0.0179 |
| ARHGEF3 | −1.32 | 0.0088 |
| TCF7L2 | −1.29 | 0.0063 |
| JAK2 | −1.29 | 0.0208 |
| CTSL | −1.28 | 0.0165 |
| CLCN6 | −1.26 | 0.0351 |
| BLZF1 | −1.26 | 0.0017 |
| IL6ST | −1.25 | 0.0094 |
| GTPBP1 | −1.24 | 0.0002 |
| ALCAM | −1.24 | 0.0257 |
| GOLGA3 | −1.24 | 0.0019 |
| PPIC | −1.23 | 0.0273 |
| USP25 | −1.22 | 0.0497 |
| PLOD2 | −1.22 | 0.0161 |
| CHST12 | −1.21 | 0.0233 |
| PSCD1 | −1.21 | 0.0004 |
| KDELR2 | −1.19 | 0.0006 |
| SMAD3 | −1.19 | 0.0344 |
| JAK1 | −1.17 | 0.0411 |
| ZNF24 | −1.16 | 0.0411 |
| BTG1 | −1.16 | 0.0471 |
| MCL1 | −1.16 | 0.0127 |
| MTMR1 | −1.14 | 0.0117 |
| KPNB1 | −1.12 | 0.0098 |
| YWHAE | −1.11 | 0.0421 |
| PCMT1 | −1.10 | 0.0351 |
| RANBP1 | 1.13 | 0.0297 |
| GLUL | 1.13 | 0.0013 |
| MYD88 | 1.15 | 0.0364 |
| CHD6 | 1.16 | 0.0032 |
| GCH1 | 1.17 | 0.0189 |
| VAT1 | 1.21 | 0.0142 |
| PDGFA | 1.23 | 0.0495 |
| PTEN | 1.23 | 0.0253 |
| BAG1 | 1.26 | 0.0044 |
| IRF3 | 1.26 | 0.0349 |
| PSMA2 | 1.27 | 0.0148 |
| IL28RA | 1.28 | 0.0266 |
| GTF2F1 | 1.28 | 0.0237 |
| PEX26 | 1.29 | 0.0370 |
| DRAP1 | 1.29 | 0.0011 |
| ZFYVE26 | 1.31 | 0.0096 |
| LIFR | 1.33 | 0.0279 |
| RBCK1 | 1.34 | 0.0199 |
| DNAPTP6 | 1.34 | 0.0304 |
| SSBP3 | 1.35 | 0.0121 |
| TNFSF13B | 1.36 | 0.0200 |
| TRIM14 | 1.36 | 0.0030 |
| TBX3 | 1.42 | 0.0070 |
| GNAI1 | 1.43 | 0.0488 |
| PCGF2 | 1.44 | 0.0148 |
| RXRA | 1.46 | 0.0187 |
| SLC25A30 | 1.53 | 0.0499 |
| TRIM26 | 1.56 | 0.0014 |
| PCTK3 | 1.59 | 0.0160 |
| CXCL10 | 1.71 | 0.0140 |
| EHHADH | 1.80 | 0.0196 |
| IFIT3 | 1.88 | 0.0439 |
| SDC2 | 1.96 | 0.0313 |
| CRYM | 2.03 | 0.0313 |
| MAFB | 2.60 | 0.0157 |
| PADI2 | 2.66 | 0.0045 |
| CX3CL1 | 2.73 | 0.0317 |
| LEPR | 2.89 | 0.0058 |
| FBXO6 | 3.00 | 0.0042 |
| AKAP12 | 3.33 | 0.0291 |
| IFIT1 | 3.58 | 0.0062 |
| C4orf33 | 3.95 | 0.0173 |
| SOAT2 | 4.03 | 0.0043 |
| G6PC | 4.22 | 0.0001 |
| RHOH | 5.26 | 0.0270 |
| BHMT | 5.84 | 0.0082 |

DAY 7

| Gene_Symbol | Raw Est Fold Change | Unadjusted p-value |
|---|---|---|
| STEAP4 | −1275.83 | 0.0037 |
| CRP | −63.77 | 0.0011 |
| CD38 | −60.43 | 0.0007 |
| CASP4 | −43.41 | 0.0077 |
| SOCS1 | −42.96 | 0.0011 |
| EREG | −21.64 | 0.0383 |
| AMPH | −21.01 | 0.0152 |
| SOCS3 | −17.74 | 0.0017 |
| IFITM1 | −15.75 | 0.0016 |
| CD300LF | −15.50 | 0.0020 |
| TIMP1 | −11.92 | 0.0017 |
| CASP5 | −11.12 | 0.0299 |
| IFI16 | −11.00 | 0.0002 |
| IER3 | −9.69 | 0.0042 |
| IL8 | −9.22 | 0.0105 |
| PHLDA1 | −9.08 | 0.0062 |
| ICAM1 | −9.02 | 0.0003 |
| JUNB | −8.16 | 0.0001 |
| CYR61 | −7.93 | 0.0147 |
| EFNB2 | −7.87 | 0.0002 |
| TXNIP | −7.72 | 0.0042 |
| MYC | −7.27 | 0.0002 |
| CEBPD | −6.95 | 0.0000 |
| THBD | −6.70 | 0.0048 |
| C10orf10 | −6.70 | 0.0078 |
| CYP1B1 | −6.56 | 0.0033 |
| TEAD4 | −6.47 | 0.0013 |
| GALNT2 | −6.32 | 0.0059 |
| MAP3K8 | −6.22 | 0.0006 |
| NFE2 | −5.79 | 0.0110 |
| CSDA | −5.60 | 0.0046 |
| ID1 | −5.53 | 0.0022 |
| ITGA2 | −5.40 | 0.0038 |
| AKT3 | −5.29 | 0.0145 |
| MTHFD2L | −5.12 | 0.0053 |
| RAB27A | −5.10 | 0.0009 |
| EGR1 | −4.88 | 0.0050 |
| HIF1A | −4.78 | 0.0027 |
| IFITM2 | −4.71 | 0.0010 |
| CREB3L3 | −4.65 | 0.0011 |
| GBP2 | −4.50 | 0.0048 |
| NPAS2 | −4.43 | 0.0028 |
| KIF5C | −4.32 | 0.0252 |
| CCND3 | −4.18 | 0.0317 |
| ULK4 | −4.12 | 0.0349 |
| HEG1 | −4.07 | 0.0126 |
| STAT1 | −4.03 | 0.0004 |
| CTGF | −3.88 | 0.0200 |
| MYT1 | −3.88 | 0.0037 |
| ADM | −3.85 | 0.0014 |
| IFNGR1 | −3.76 | 0.0001 |
| CD3D | −3.72 | 0.0338 |
| C4BPA | −3.52 | 0.0129 |
| AKR1B1 | −3.52 | 0.0468 |
| RBMS1 | −3.48 | 0.0157 |

TABLE 1-continued

| Gene | Value | P-value |
|---|---|---|
| IRF7 | −3.42 | 0.0007 |
| ETV7 | −3.42 | 0.0091 |
| ARHGDIB | −3.40 | 0.0073 |
| NLRC5 | −3.27 | 0.0271 |
| HK2 | −3.18 | 0.0001 |
| PDGFRL | −3.16 | 0.0005 |
| BCL3 | −3.15 | 0.0049 |
| TMEM2 | −3.07 | 0.0017 |
| CFB | −2.96 | 0.0419 |
| LTBP2 | −2.94 | 0.0244 |
| HPSE | −2.92 | 0.0055 |
| LRP4 | −2.80 | 0.0161 |
| ARHGEF3 | −2.76 | 0.0073 |
| PHF11 | −2.75 | 0.0010 |
| BLVRA | −2.70 | 0.0040 |
| IKZF2 | −2.69 | 0.0036 |
| TNFSF14 | −2.68 | 0.0089 |
| HBE1 | −2.67 | 0.0354 |
| PIM3 | −2.64 | 0.0002 |
| C1R | −2.64 | 0.0321 |
| SPSB1 | −2.63 | 0.0444 |
| IQGAP1 | −2.60 | 0.0069 |
| PLSCR1 | −2.59 | 0.0087 |
| IL1RN | −2.59 | 0.0490 |
| PML | −2.58 | 0.0290 |
| PLAUR | −2.56 | 0.0069 |
| CD47 | −2.51 | 0.0031 |
| B4GALT5 | −2.50 | 0.0019 |
| FER1L3 | −2.43 | 0.0270 |
| HLA-DMA | −2.39 | 0.0064 |
| GK | −2.38 | 0.0221 |
| NEXN | −2.35 | 0.0251 |
| PPIC | −2.26 | 0.0023 |
| ATP10D | −2.21 | 0.0020 |
| ETS2 | −2.17 | 0.0003 |
| AHR | −2.08 | 0.0469 |
| ABHD5 | −2.05 | 0.0003 |
| EWSR1 | −2.03 | 0.0011 |
| FNDC3B | −2.02 | 0.0010 |
| TAP2 | −2.02 | 0.0010 |
| C1S | −2.00 | 0.0143 |
| TMEM49 | −1.98 | 0.0047 |
| UBE2S | −1.95 | 0.0129 |
| MAX | −1.95 | 0.0013 |
| SLFN12 | −1.92 | 0.0054 |
| CAPN2 | −1.90 | 0.0461 |
| STK39 | −1.88 | 0.0183 |
| FAM102A | −1.88 | 0.0192 |
| ETV6 | −1.87 | 0.0008 |
| SERPINB9 | −1.86 | 0.0373 |
| IRF8 | −1.86 | 0.0014 |
| EPAS1 | −1.83 | 0.0015 |
| IL6ST | −1.83 | 0.0003 |
| TFPI | −1.80 | 0.0062 |
| B2M | −1.77 | 0.0444 |
| KIAA0040 | −1.76 | 0.0171 |
| IFITM3 | −1.73 | 0.0047 |
| ATP1B3 | −1.72 | 0.0096 |
| TAP1 | −1.72 | 0.0376 |
| LYN | −1.71 | 0.0031 |
| SSR1 | −1.71 | 0.0054 |
| MAFK | −1.70 | 0.0155 |
| PHF15 | −1.69 | 0.0002 |
| RECQL | −1.66 | 0.0266 |
| IMPA2 | −1.62 | 0.0124 |
| NFIL3 | −1.60 | 0.0293 |
| CHST12 | −1.59 | 0.0001 |
| SFPQ | −1.57 | 0.0026 |
| ZC3HAV1 | −1.57 | 0.0354 |
| TCF7L2 | −1.57 | 0.0205 |
| SLC15A2 | −1.52 | 0.0082 |
| SAA1 | −1.51 | 0.0118 |
| WARS | −1.50 | 0.0343 |
| SPTLC2 | −1.49 | 0.0401 |
| HERC6 | −1.49 | 0.0074 |
| IL1R2 | −1.48 | 0.0443 |
| SLC25A28 | −1.47 | 0.0437 |
| CD164 | −1.47 | 0.0227 |
| ALCAM | −1.46 | 0.0057 |
| PCMT1 | −1.45 | 0.0495 |
| RIPK2 | −1.45 | 0.0285 |
| PTEN | −1.44 | 0.0119 |
| PUS1 | −1.41 | 0.0014 |
| TOR1B | −1.39 | 0.0059 |
| PON2 | −1.39 | 0.0034 |
| GNB1 | −1.39 | 0.0211 |
| FLT1 | −1.38 | 0.0483 |
| GRN | −1.37 | 0.0031 |
| HDAC2 | −1.34 | 0.0170 |
| KPNB1 | −1.34 | 0.0001 |
| MCL1 | −1.33 | 0.0009 |
| GLB1 | −1.33 | 0.0347 |
| RAN | −1.29 | 0.0126 |
| PXK | −1.23 | 0.0286 |
| FGG | −1.22 | 0.0437 |
| MTMR1 | −1.20 | 0.0011 |
| TARBP1 | −1.18 | 0.0376 |
| ZNF24 | −1.16 | 0.0322 |
| EIF2AK2 | −1.14 | 0.0109 |
| MYD88 | 1.19 | 0.0373 |
| SF3A1 | 1.26 | 0.0281 |
| TFDP2 | 1.26 | 0.0253 |
| RXRA | 1.28 | 0.0065 |
| OPTN | 1.28 | 0.0249 |
| INPP5B | 1.29 | 0.0440 |
| C6orf85 | 1.31 | 0.0357 |
| ZNF313 | 1.31 | 0.0011 |
| XRCC6BP1 | 1.33 | 0.0068 |
| BAG1 | 1.33 | 0.0124 |
| PARP14 | 1.33 | 0.0439 |
| NMI | 1.34 | 0.0171 |
| APOL6 | 1.36 | 0.0037 |
| IRF1 | 1.36 | 0.0103 |
| PEX26 | 1.38 | 0.0419 |
| IL17RB | 1.38 | 0.0313 |
| JAK2 | 1.39 | 0.0180 |
| CASP1 | 1.40 | 0.0364 |
| PI4K2B | 1.41 | 0.0128 |
| SHMT2 | 1.44 | 0.0008 |
| ZNF276 | 1.44 | 0.0257 |
| BRF2 | 1.46 | 0.0432 |
| IFIH1 | 1.47 | 0.0203 |
| SSBP3 | 1.49 | 0.0092 |
| CPT1A | 1.49 | 0.0121 |
| COL16A1 | 1.53 | 0.0188 |
| ALDH1A1 | 1.54 | 0.0115 |
| IL28RA | 1.55 | 0.0243 |
| MYOM2 | 1.59 | 0.0015 |
| ASNS | 1.63 | 0.0019 |
| SCARB2 | 1.64 | 0.0454 |
| UBE1L | 1.65 | 0.0253 |
| C4orf33 | 1.65 | 0.0090 |
| SDC2 | 1.66 | 0.0134 |
| TRIM14 | 1.68 | 0.0146 |
| CREM | 1.71 | 0.0115 |
| TPM1 | 1.77 | 0.0064 |
| SLC7A5 | 1.78 | 0.0089 |
| ACSL1 | 1.78 | 0.0242 |
| EIF2S2 | 1.81 | 0.0059 |
| GCH1 | 1.83 | 0.0034 |
| USP25 | 1.84 | 0.0201 |
| TRIB3 | 1.84 | 0.0317 |
| ITGA6 | 1.89 | 0.0133 |
| SLC20A1 | 1.90 | 0.0164 |
| PSMB10 | 1.91 | 0.0055 |
| GPR171 | 1.93 | 0.0497 |
| SRGAP2 | 1.95 | 0.0118 |
| ISOC1 | 1.96 | 0.0400 |
| NGFB | 1.97 | 0.0265 |
| CCL19 | 2.16 | 0.0359 |
| PCTK3 | 2.27 | 0.0242 |
| GBP3 | 2.28 | 0.0015 |
| DHFR | 2.31 | 0.0055 |
| SAMD9L | 2.42 | 0.0019 |
| AGXT | 2.54 | 0.0066 |
| F3 | 2.54 | 0.0090 |
| CLEC2D | 2.54 | 0.0085 |
| MT1F | 2.56 | 0.0347 |
| FCGR1A | 2.56 | 0.0338 |
| EMP1 | 2.60 | 0.0241 |

TABLE 1-continued

| | | |
|---|---|---|
| DNAPTP6 | 2.61 | 0.0167 |
| SLC30A1 | 2.66 | 0.0129 |
| IFIT3 | 2.91 | 0.0014 |
| CKB | 2.95 | 0.0079 |
| HESX1 | 3.01 | 0.0169 |
| RPL22 | 3.02 | 0.0043 |
| CXCL11 | 3.15 | 0.0489 |
| WAS | 3.44 | 0.0054 |
| GLUL | 3.54 | 0.0002 |
| CRYM | 3.57 | 0.0035 |
| HAO1 | 3.59 | 0.0350 |
| FBXO6 | 3.59 | 0.0003 |
| HLA-DOA | 3.70 | 0.0240 |
| IGHM | 3.80 | 0.0153 |
| SELL | 3.83 | 0.0060 |
| FAM70A | 4.10 | 0.0037 |
| PADI2 | 4.13 | 0.0004 |
| CLEC4E | 4.33 | 0.0139 |
| CD163 | 4.54 | 0.0465 |
| CD9 | 4.66 | 0.0392 |
| PON1 | 5.18 | 0.0007 |
| PLAC8 | 5.43 | 0.0070 |
| RSAD2 | 5.52 | 0.0001 |
| AXL | 5.52 | 0.0299 |
| SELP | 5.95 | 0.0437 |
| G6PC | 6.12 | 0.0086 |
| MAFB | 6.31 | 0.0007 |
| EHHADH | 6.99 | 0.0047 |
| TFEC | 7.83 | 0.0320 |
| PCK2 | 8.00 | 0.0043 |
| CX3CR1 | 9.27 | 0.0030 |
| SLC10A1 | 10.61 | 0.0012 |
| SOAT2 | 11.97 | 0.0016 |
| MSR1 | 16.00 | 0.0299 |
| IFIT1 | 16.72 | 0.0004 |
| UPP2 | 16.78 | 0.0093 |
| BHMT | 100.46 | 0.0000 |

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$-$R^{11}$ of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety.

The term "optionally substituted" refers to the fact that one or more hydrogen atoms of a moiety (with one or more hydrogen atoms) can be, but does not necessarily have to be, substituted with another substituent.

The term "halogen" refers to a moiety of fluoro, chloro, bromo or iodo.

Unless otherwise indicated, the term "hydrogen" or "hydro" refers to the moiety of a hydrogen atom (—H) and not $H_2$.

The term in iCell hepatocytes refers to induced pluripotent stem cell derived hepatocytes from Cellular Dynamics International (CDI).

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula I). The compounds of the present invention can also be solvated, i.e. hydrated. The solvation can be effected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

In detail, the present invention relates to the compounds of formula I:

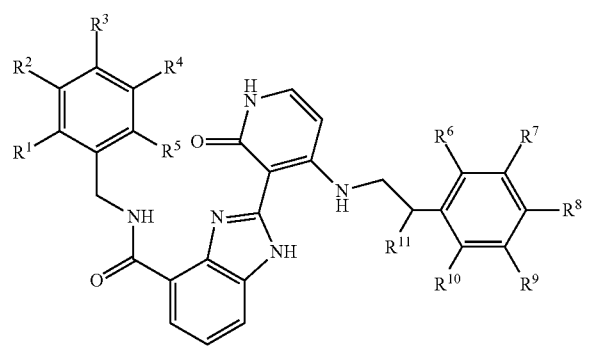

and pharmaceutically acceptable salts and esters thereof, wherein $R^1$, $R^2$, $R^3$, $R^4$, $R^5$, $R^6$, $R^7$, $R^8$, $R^9$, and $R^{10}$ are independently hydrogen or halogen; and $R^{11}$ is hydrogen or hydroxy. Unless indicated otherwise, the compounds within the genus of formula I encompass all possible stereoisomers (i.e., (R)-enantiomers, (S)-enantiomers) as well as racemic and scalemic mixtures thereof.

In one embodiment, $R^1$, $R^2$, $R^3$, $R^4$, and $R^5$ are all hydrogen. In another embodiment, at least one of $R^1$, $R^2$, $R^3$, $R^4$, or $R^5$ is halogen. In another embodiment, at least one of $R^1$, $R^2$, $R^3$, $R^4$, or $R^5$ is fluoro. In another embodiment, $R^1$, $R^3$, and $R^5$ are all hydrogen and one of $R^2$ or $R^4$ is fluoro and the other is hydrogen.

In another particular embodiment, $R^6$, $R^7$, $R^8$, $R^9$, and $R^{10}$ are all hydrogen. In another embodiment, at least one of $R^6$, $R^7$, $R^8$, $R^9$, and $R^{10}$ is halogen. In another embodiment, at least one of $R^6$, $R^7$, $R^8$, $R^9$, and $R^{10}$ is chloro. In another embodiment, $R^6$, $R^8$, and $R^{10}$ are all hydrogen and one of $R^7$ or $R^9$ is chloro and the other is hydrogen.

In one embodiment, $R^{11}$ is hydrogen. In a more specific embodiment one of $R^1$, $R^2$, $R^3$, $R^4$, or $R^5$ is halogen (preferably fluoro) and the others hydrogen; and $R^6$, $R^7$, $R^8$, $R^9$, $R^{10}$, and $R^{11}$ are hydrogen.

In another embodiment, $R^{11}$ is hydroxy. In a more specific embodiment one of $R^1$, $R^2$, $R^3$, $R^4$, or $R^5$ is halogen (preferably fluoro) and the others hydrogen; $R^6$, $R^7$, $R^8$, $R^9$, and $R^{10}$ are hydrogen, and $R^{11}$ is hydroxy.

In one embodiment, the present invention relates to the compounds of formula IA:

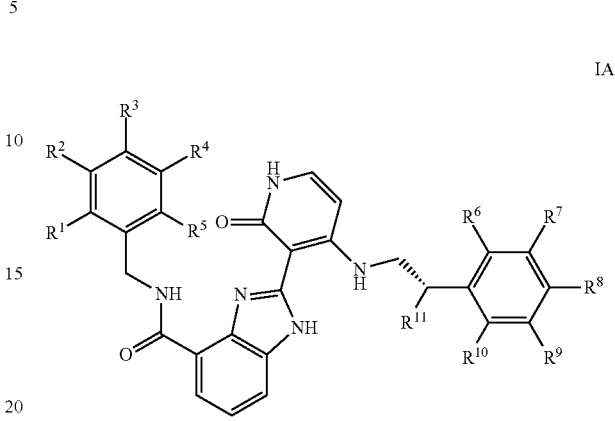

and pharmaceutically acceptable salts and esters thereof, wherein $R^1$, $R^2$, $R^3$, $R^4$, $R^5$, $R^6$, $R^7$, $R^8$, $R^9$, and $R^{10}$ are independently hydrogen or halogen; and $R^{11}$ is hydroxy.

In another embodiment, the present invention relates to the compounds of formula IB:

IB and pharmaceutically acceptable salts and esters thereof, wherein $R^1$, $R^2$, $R^3$, $R^4$, $R^5$, $R^6$, $R^7$, $R^8$, $R^9$, and $R^{10}$ are independently hydrogen or halogen; and $R^{11}$ is hydroxy.

In one embodiment, the present invention relates to a compound of the formula:

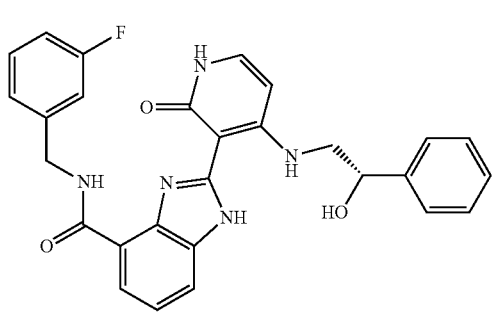

In another embodiment, the present invention relates to a compound of the formula:

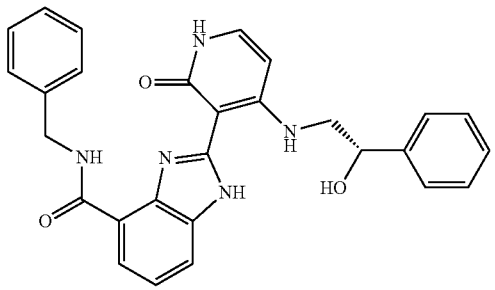

In another embodiment, the present invention relates to a compound of the formula:

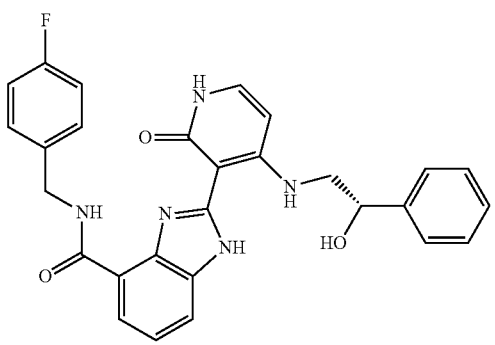

In another embodiment, the present invention relates to a compound of the formula:

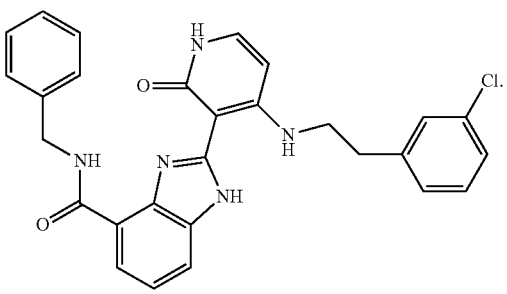 [SMILES: O=C(NCc1ccccc1)c1cccc2[nH]c(-c3c(NCCc4cccc(Cl)c4)cc[nH]c3=O)nc12]

In another embodiment, the present invention relates to a compound of the formula:

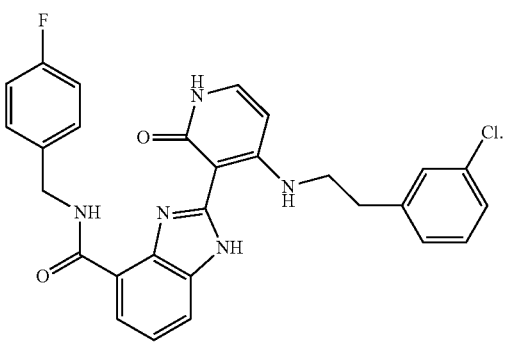 [SMILES: O=C(NCc1ccc(F)cc1)c1cccc2[nH]c(-c3c(NCCc4cccc(Cl)c4)cc[nH]c3=O)nc12]

In another embodiment, the present invention relates to a compound of the formula:

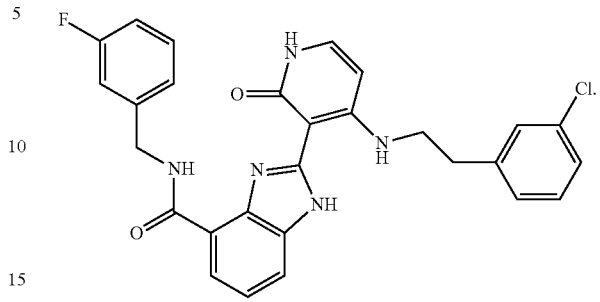

In another embodiment, the present invention relates to a compound of the formula:

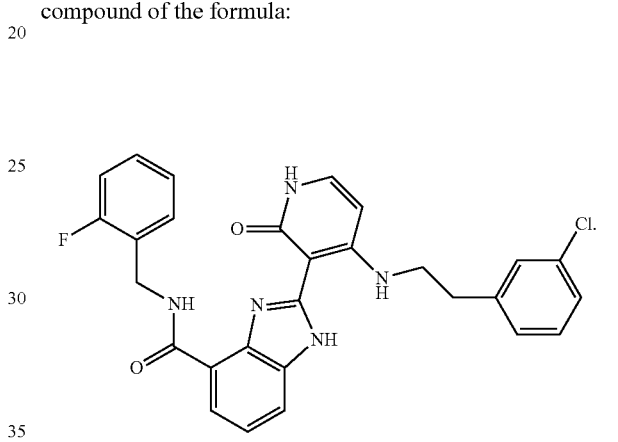

The starting materials and reagents used in preparing these compounds generally are either available from commercial suppliers, such as Aldrich Chemical Co., or are prepared by methods known to those skilled in the art. The following synthetic reaction schemes are merely illustrative of some methods by which the compounds of the present invention can be synthesized, and various modifications to these synthetic reaction schemes can be made and will be suggested to one skilled in the art. Further exemplification can be found in the specific examples.

The compounds of the present invention can be prepared by any conventional means. Suitable processes for synthesizing these compounds are provided in the examples. Generally, compounds of formula I can be prepared according to the schemes illustrated below.

Scheme 1

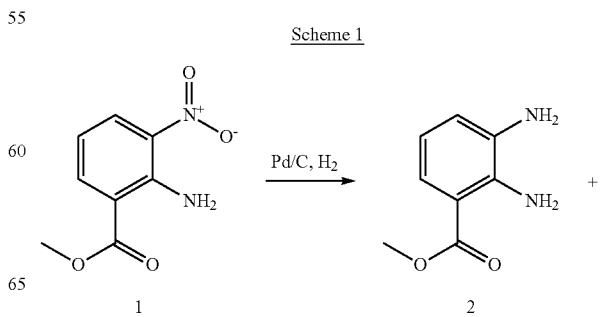

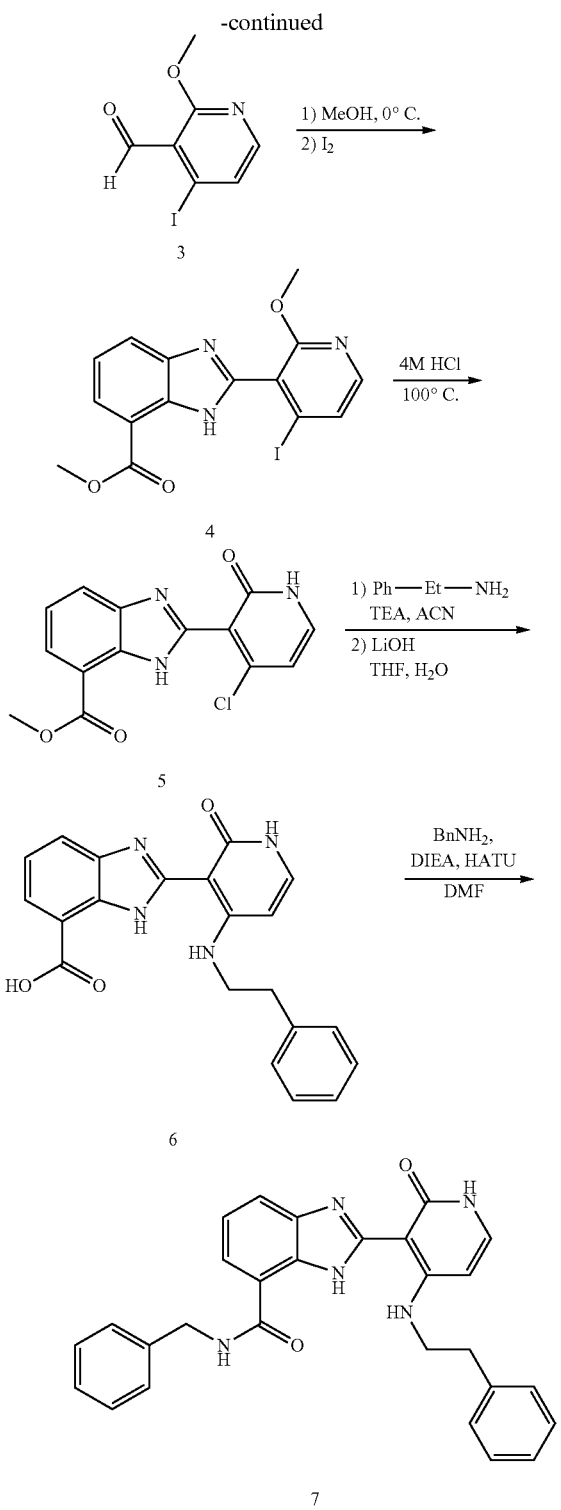

for several hours. The aryl chloride of compound 5 can be displaced with 2-phenyl-ethylamines through nucleophilic aromatic substitutions with a base like triethylamine or N-methylmorpholine in a polar solvent like acetonitrile or N,N-dimethylformamide and heat for several hours. The resulting compound can be de-esterified using standard methods like lithium hydroxide in tetrahydrofuran and water and mild heat to yield the benzoimidazole carboxyl acid 6. The final compounds like 7 can be prepared by condensation of the acid 6 and with benzyl amines through standard amide coupling conditions like N,N-diisopropyl-ethylamine, and O-(7-azabenzotriazol-1-yl)-N,N,N',N-tetramethyluronium hexafluorophosphate in a polar solvent like dimethylformamide (DMF).

EXAMPLES

Although certain exemplary embodiments are depicted and described herein, the compounds of the present invention can be prepared using appropriate starting materials according to the methods described generally herein and/or by methods available to one of ordinary skill in the art.

Example 1

Synthesis of 2-[4-((S)-2-hydroxy-2-phenyl-ethylamino)-2-oxo-1,2-dihydro-pyridin-3-yl]-3H-benzoimidazole-4-carboxylic acid 3-fluoro-benzylamide 2-(4-Iodo-2-methoxy-pyridin-3-yl)-3H-benzoimidazole-4-carboxylic acid Methyl ester

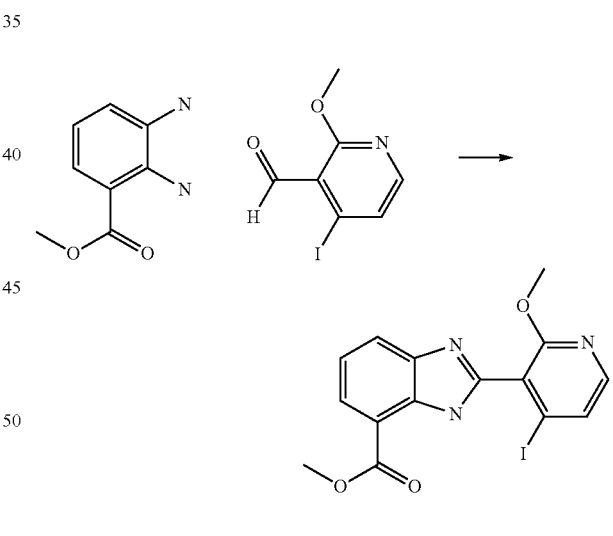

Starting with the methyl diaminobenzoate 2, which can be commercially available or prepared from the reduction of the nitro compound 1 with hydrogen and paladium on carbon, can be condensed with the pyridine aldehyde 3 and subsequently oxidized in situ with iodine to produce the benzoimidazole 4. The 2-methoxy-3-iodo-pyridine moiety of the benzoimidazole can be converted to the 3-chloro-pyrmidone 5 with 4 M hydrochloric acid in dioxane and heating to 100° C.

In a 250 mL round-bottomed flask, methyl 2,3-diaminobenzoate (1.5 g, 9.03 mmol) was combined with methanol (25 mL) to give a yellow solution that was stirred under nitrogen and cooled in a water/dry ice bath. To this was added drop wise 4-iodo-2-methoxynicotinaldehyde (2.37 g, 9.03 mmol) dissolved in methanol (15 mL) and DMF (10 mL). During the addition more methanol (25.0 mL) was added to the reaction. The reaction was kept in the water/dry ice bath for 2.5 hr, allowed to warm to room temperature over 3 hr, and then cooled in a water/dry ice bath. To this was added drop wise iodine (1.49 g, 5.87 mmol) dissolved in methanol (15 mL) and then the reaction was allowed to warm to room temperature overnight. The reaction was concentrated, diluted with ethyl acetate (200 mL) and saturated Na$_2$S$_2$O$_3$ (200 mL) and mixed. Significant insoluble material was present and the mixture was filtered. The resulting solid was washed with ethyl acetate and water. The filtrate was separated and the resulting aqueous layer was extracted with ethyl acetate (100 mL) and DCM (3×150 mL). The organic layers were washed with saturated Na$_2$S$_2$O$_3$ and brine, combined, dried over MgSO4, and concentrated as a red oil/solid. The insoluble solid from the original extract was washed with DCM (5×100 mL) and the filtrate was concentrated as a dark red/black solid. The liquid extracted crude and the solid extract crude were dissolved in minimal DCM, combined, and purified by flash chromatography (silica gel, 120 g, 0% to 60% ethyl acetate in hexanes) to give 2-(4-iodo-2-methoxy-pyridin-3-yl)-3-H-benzoimidazole-4-carboxylic acid methyl ester, as a purple solid, 0.73 g LC/MS calcd for C$_{15}$H$_{12}$IN$_3$O$_3$ (m/e) 409.0, obsd 410.0 (M+H); $^1$H NMR (DMSO-d$_6$) δ: 12.68 (s, 1H), 8.05 (d, J=5.5 Hz, 1H), 8.01 (d, J=8.0 Hz, 1H), 7.88-7.95 (m, 1H), 7.67 (d, J=5.3 Hz, 1H), 7.38 (t, J=7.9 Hz, 1H), 3.96 (s, 3H), 3.82 (s, 3H). The original insoluble solid remaining after being extracted with DCM was subsequently extracted with boiling methanol (5×20 ml). The methanol filtrate was concentrated and dried, yielding additional product (83% pure by LCMS), as the sodium salt (assumed) and as a dark purple solid, 0.57 g. The remaining original insoluble solid after the DCM and methanol extractions yielded additional product (90% pure by LCMS), as the sodium salt (assumed) and as a purple solid, 0.88 g. The combined yield was 59%.

2-(4-Chloro-2-oxo-1,2-dihydro-pyridin-3-yl)-3H-benzoimidazole-4-carboxylic acid methyl ester Two reactions were initially done in parallel and were combined prior to heating. (In a 200 mL round-bottomed flask 2-(4-iodo-2-methoxy-pyridin-3-yl)-3H-benzoimidazole-4-carboxylic acid methyl ester (solid isolated from liquid extraction) (0.88 g, 2.15 mmol) was combined with 1,4-dioxane (3 mL) to give a black suspension, 4 M HCl in 1,4-dioxane (14.5 mL, 58.1 mmol) was added portion wise, and mixture was stirred at room temperature, 17 hr. In a 200 mL round-bottomed flask, methyl 2-(4-iodo-2-methoxy-pyridin-3-yl)-3H-benzoimidazole-4-carboxylic acid methyl ester (isolated from flash chromatography) (0.73 g, 1.78 mmol) was combined with 1,4-dioxane (2 mL) to give a black suspension, 4 M HCl in 1,4-dioxane (12 mL, 48.2 mmol) was added, and the mixture was stirred at room temperature, 17 hr.) The separate reactions were combined with addition of 1,4-dioxane (for rinsing) and 4 M HCl in 1,4-dioxane (20 mL). The reaction was heated in an oil bath at 100° C. for 3 hr and then allowed to cool to room temperature. The reaction was filtered, and the solid was washed with 1,4-dioxane, water, 1,4-dioxane, hexanes, and dried over house vacuum yielding 2-(4-chloro-2-oxo-1,2-dihydro-pyridin-3-yl)-3H-benzoimidazole-4-carboxylic acid methyl ester (0.91 g, 76.2% yield) as a black solid. LC/MS calcd for C$_{14}$H$_{10}$ClN$_3$O$_3$ (m/e) 303.0, obsd 304.1 (M+H); $^1$H NMR (DMSO-d$_6$) δ: 8.05-8.16 (m, 2H), 8.01 (d, J=7.3 Hz, 1H), 7.66-7.76 (m, 1H), 7.50 (t, J=7.9 Hz, 1H), 3.92-4.04 (m, 3H).

2-[4-((S)-2-Hydroxy-2-phenyl-ethylamino)-2-oxo-1,2-dihydro-pyridin-3-yl]-3H-benzoimidazole-4-carboxylic acid methyl ester

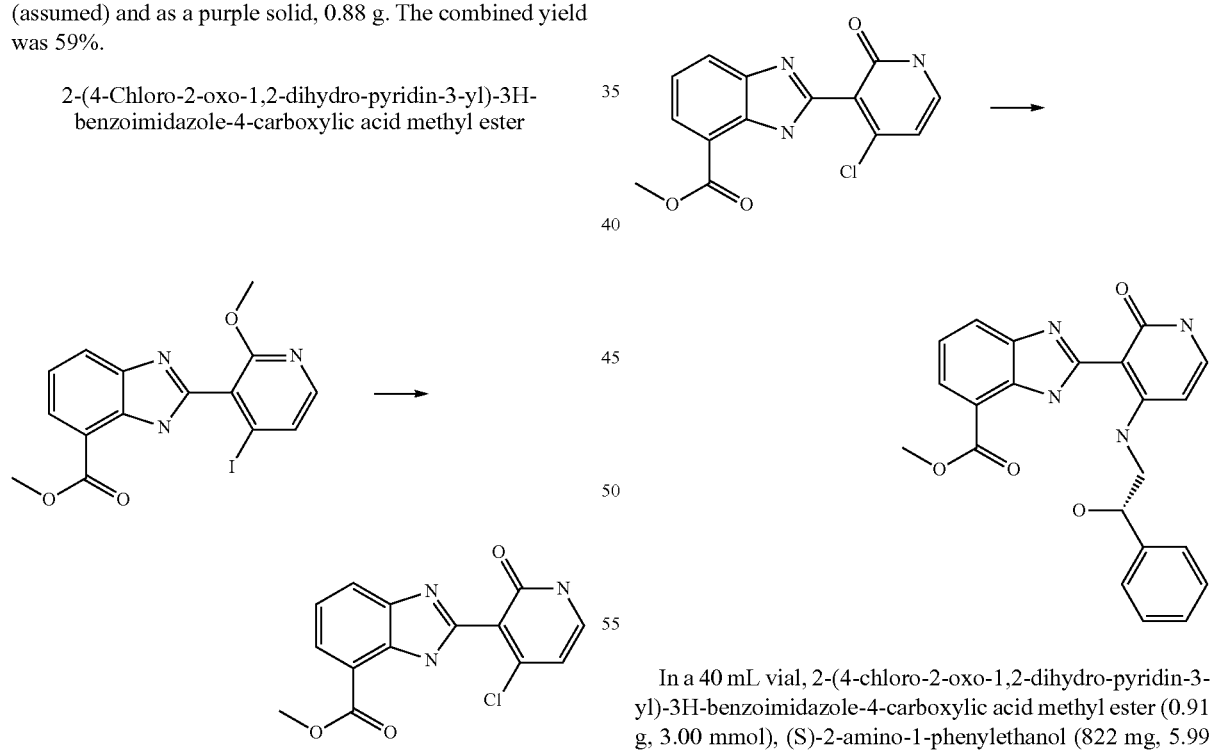

In a 40 mL vial, 2-(4-chloro-2-oxo-1,2-dihydro-pyridin-3-yl)-3H-benzoimidazole-4-carboxylic acid methyl ester (0.91 g, 3.00 mmol), (S)-2-amino-1-phenylethanol (822 mg, 5.99 mmol) and N-methylmorpholine (909 mg, 988 μL, 8.99 mmol) were combined with DMF (20 mL) to give a black suspension. The vial was sealed and heated in a dry block at 85° C. for 6.5 hr and allowed to cool to room temperature over the weekend. The reaction was diluted with water and the resulting precipitate was washed with water and hexanes yielding 2-[4-((S)-2-hydroxy-2-phenyl-ethylamino)-2-oxo- 1,2-dihydro-pyridin-3-yl]-3H-benzoimidazole-4-carboxylic acid methyl ester (0.87 g, 71.8% yield) as a light purple solid. LC/MS calcd for $C_{22}H_{20}N_4O_4$ (m/e) 404.0, obsd 405.2 (M+H); $^1$H NMR (DMSO-$d_6$) δ: 13.53 (s, 1H), 11.26 (d, J=5.8 Hz, 1H), 10.85 (t, J=5.1 Hz, 1H), 7.85 (d, J=8.0 Hz, 1H), 7.76-7.82 (m, 1H), 7.55 (d, J=7.3 Hz, 2H), 7.34-7.42 (m, 3H), 7.26-7.34 (m, 2H), 6.22 (d, J=7.5 Hz, 1H), 5.80 (d, J=4.5 Hz, 1H), 4.85-5.00 (m, 1H), 3.98 (s, 3H), 3.64-3.77 (m, 1H), 3.53-3.63 (m, 1H).

2-[4-((S)-2-Hydroxy-2-phenyl-ethylamino)-2-oxo-1, 2-dihydro-pyridin-3-yl]-3H-benzoimidazole-4-carboxylic acid

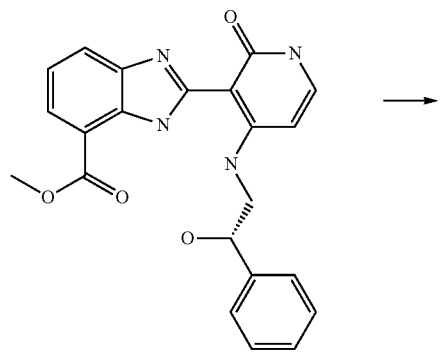

In a 200 mL round-bottomed flask, 2-[4-((S)-2-hydroxy-2-phenyl-ethylamino)-2-oxo-1,2-dihydro-pyridin-3-yl]-3H-benzoimidazole-4-carboxylic acid methyl ester (0.87 g, 2.15 mmol) and LiOH (258 mg, 10.8 mmol) were combined with THF (20 mL1) and Water (5 mL) to give a purple suspension. The reaction was stirred at room temperature overnight. The next day the reaction was heated in dry block at 50° C. for 3.5 hr and cooled to room temperature. The reaction was dilute with water, concentrated, dilute with more water, and acidify with 1M HCl, and filtered. The resulting solid was washed with water and hexanes, and dried over house vacuum yielding 2-[4-((S)-2-hydroxy-2-phenyl-ethylamino)-2-oxo-1,2-dihydro-pyridin-3-yl]-3H-benzoimidazole-4-carboxylic acid (0.86 g, 102% yield) as a purple solid. LC/MS calcd for $C_{21}H_{18}N_4O_4$ (m/e) 390.0, obsd 391.2 (M+H); $^1$H NMR; (DMSO-$d_6$) δ: 13.35 (s, 1H), 11.19 (d, J=6.0 Hz, 1H), 10.97 (t, J=4.9 Hz, 1H), 7.75 (dd, J=7.7, 3.9 Hz, 2H), 7.56 (d, J=7.3 Hz, 2H), 7.22-7.44 (m, 5H), 6.20 (d, J=7.5 Hz, 1H), 5.80 (br. s., 1H), 4.92 (t, J=5.5 Hz, 1H), 3.54-3.74 (m, 3H).

2-[4-((S)-2-Hydroxy-2-phenyl-ethylamino)-2-oxo-1, 2-dihydro-pyridin-3-yl]-3H-benzoimidazole-4-carboxylic acid 3-fluoro-benzylamide

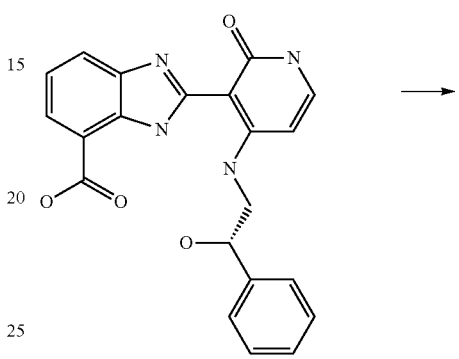

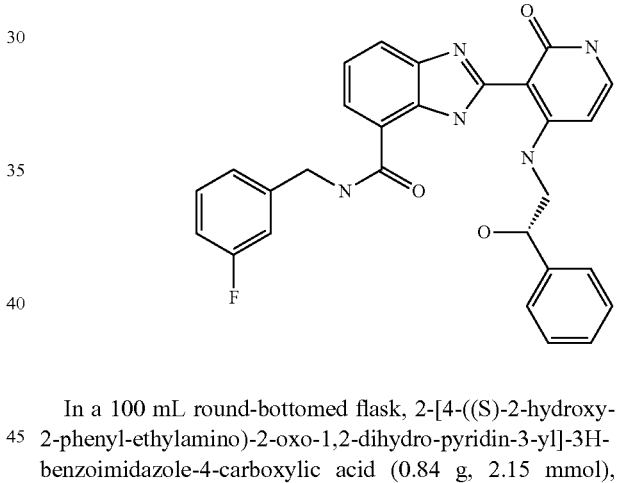

In a 100 mL round-bottomed flask, 2-[4-((S)-2-hydroxy-2-phenyl-ethylamino)-2-oxo-1,2-dihydro-pyridin-3-yl]-3H-benzoimidazole-4-carboxylic acid (0.84 g, 2.15 mmol), 3-fluoro-benzylamine (296 mg, 270 μL, 2.37 mmol) and DIEA (612 mg, 827 μL, 4.73 mmol) were combined with DMF (10 mL) to give a black solution and to this was added HATU (982 mg, 2.58 mmol). The reaction was stirred at room temperature overnight. The next day, the reaction was dripped into water and the resulting precipitate was filtered and washed with water, ethyl ether, and hexanes. The purple solid was incompletely dissolved in minimal boiling ethanol and the resulting solid that formed upon cooling was filtered and washed with ethanol and hexanes yielding 2-[4-((S)-2-hydroxy-2-phenyl-ethylamino)-2-oxo-1,2-dihydro-pyridin-3-yl]-3H-benzoimidazole-4-carboxylic acid 3-fluoro-benzylamide as a light purple solid. LC/MS calcd for $C_{28}H_{24}FN_5O_3$ (m/e) 497.0, obsd 497.9 (M+H); $^1$H NMR (DMSO-$d_6$-TFA) δ: 11.25 (br. s., 1H), 10.77 (br. s., 1H), 9.32 (t, J=5.8 Hz, 1H), 7.71-7.97 (m, 2H), 7.14-7.63 (m, 10H), 7.03-7.13 (m, 1H), 6.21 (d, J=7.5 Hz, 1H), 4.84 (br. s., 1H), 4.68 (br. s., 2H), 3.65 (d, J=12.5 Hz, 1H), 3.46 (d, J=7.0 Hz, 1H).

Example 2

Synthesis of 2-[4-((S)-2-Hydroxy-2-phenyl-ethylamino)-2-oxo-1,2-dihydro-pyridin-3-yl]-3H-benzoimidazole-4-carboxylic acid benzylamide

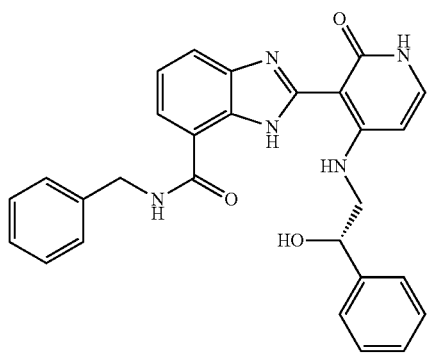 [SMILES: O=C(NCc1ccccc1)c1cccc2nc(-c3c(NC[C@@H](O)c4ccccc4)cc[nH]c3=O)[nH]c12]

2-[4-((S)-2-Hydroxy-2-phenyl-ethylamino)-2-oxo-1,2-dihydro-pyridin-3-yl]-3H-benzoimidazole-4-carboxylic acid benzylamide was synthesized from 2-[4-((S)-2-hydroxy-2-phenyl-ethylamino)-2-oxo-1,2-dihydro-pyridin-3-yl]-3H-benzoimidazole-4-carboxylic acid, benzylamine, DIEA, HATU and DMF using a similar procedure as 2-[4-((S)-2-hydroxy-2-phenyl-ethylamino)-2-oxo-1,2-dihydro-pyridin-3-yl]-3H-benzoimidazole-4-carboxylic acid 3-fluoro-benzylamide yielding 2-[4-((S)-2-hydroxy-2-phenyl-ethylamino)-2-oxo-1,2-dihydro-pyridin-3-yl]-3H-benzoimidazole-4-carboxylic acid benzylamide. LC/MS calcd for $C_{28}H_{25}N_5O_3$ (m/e) 479.0, obsd 480 (M+H). $^1$H NMR (tautomers 1:2; DMSO-$d_6$) δ: 13.38-13.52 (m, 1H), 11.14-11.38 (m, 1H), 10.33-11.02 (m, 1H), 9.18-9.43 (m, 1H), 7.69-7.99 (m, 2H), 7.15-7.61 (m, 12H), 6.12-6.30 (m, 1H), 5.74-5.99 (m, 1H), 4.52-4.96 (m, 3H), 3.49-3.30 (m, 2H).

Example 3

Synthesis of 2-[4-((S)-2-Hydroxy-2-phenyl-ethylamino)-2-oxo-1,2-dihydro-pyridin-3-yl]-3H-benzoimidazole-4-carboxylic acid 4-fluoro-benzylamide

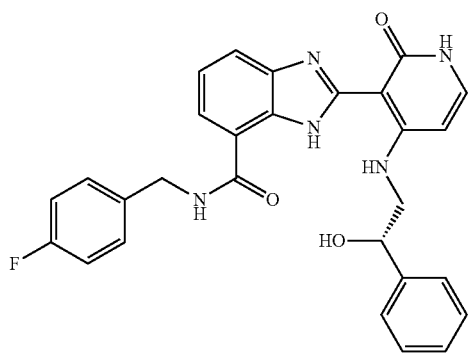 [SMILES: O=C(NCc1ccc(F)cc1)c1cccc2nc(-c3c(NC[C@@H](O)c4ccccc4)cc[nH]c3=O)[nH]c12]

2-[4-((S)-2-Hydroxy-2-phenyl-ethylamino)-2-oxo-1,2-dihydro-pyridin-3-yl]-3H-benzoimidazole-4-carboxylic acid 4-fluoro-benzylamide was synthesized from 2-[4-((S)-2-hydroxy-2-phenyl-ethylamino)-2-oxo-1,2-dihydro-pyridin-3-yl]-3H-benzoimidazole-4-carboxylic acid, benzylamine, DIEA, HATU and DMF using a similar procedure as 2-[4-((S)-2-hydroxy-2-phenyl-ethylamino)-2-oxo-1,2-dihydro-pyridin-3-yl]-3H-benzoimidazole-4-carboxylic acid 3-fluoro-benzylamide yielding 2-[4-((S)-2-hydroxy-2-phenyl-ethylamino)-2-oxo-1,2-dihydro-pyridin-3-yl]-3H-benzoimidazole-4-carboxylic acid 4-fluoro-benzylamide. LC/MS calcd for $C_{28}H_{24}FN_5O_3$ (m/e) 497.0, obsd 498 (M+H). $^1$H NMR (DMSO-$d_6$) δ: 13.35-13.53 (m, 1H), 11.13-11.38 (m, 1H), 10.35-11.03 (m, 1H), 9.19-9.42 (m, 1H), 7.68-7.97 (m, 2H), 7.24-7.58 (m, 9H), 7.08-7.22 (m, 2H), 6.13-6.30 (m, 1H), 5.74-6.02 (m, 1H), 4.49-4.98 (m, 3H), 3.49-3.29 (m, 2H).

Example 4

Synthesis of 2-{4-[2-(3-Chloro-phenyl)-ethylamino]-2-oxo-1,2-dihydro-pyridin-3-yl}-3H-benzoimidazole-4-carboxylic acid Benzylamide

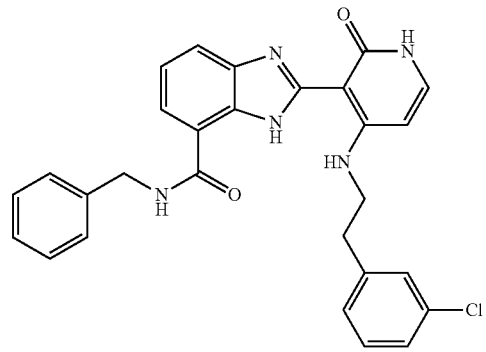 [SMILES: O=C(NCc1ccccc1)c1cccc2nc(-c3c(NCCc4cccc(Cl)c4)cc[nH]c3=O)[nH]c12]

2-{4-[2-(3-Chloro-phenyl)-ethylamino]-2-oxo-1,2-dihydro-pyridin-3-yl}-3H-benzoimidazole-4-carboxylic acid methyl ester was synthesized from 2-(4-chloro-2-oxo-1,2-dihydro-pyridin-3-yl)-3H-benzoimidazole-4-carboxylic acid methyl ester, 2-(3-Chloro-phenyl)-ethylamine, triethylamine, and ACN using a similar procedure as 2-[4-((S)-2-hydroxy-2-phenyl-ethylamino)-2-oxo-1,2-dihydro-pyridin-3-yl]-3H-benzoimidazole-4-carboxylic acid methyl ester yielding 2-{4-[2-(3-chloro-phenyl)-ethylamino]-2-oxo-1,2-dihydro-pyridin-3-yl}-3H-benzoimidazole-4-carboxylic acid methyl ester.

2-{4-[2-(3-Chloro-phenyl)-ethylamino]-2-oxo-1,2-dihydro-pyridin-3-yl}-3H-benzoimidazole-4-carboxylic acid was synthesized from 2-{4-[2-(3-chloro-phenyl)-ethylamino]-2-oxo-1,2-dihydro-pyridin-3-yl}-3H-benzoimidazole-4-carboxylic acid methyl ester, LiOH, THF, and water using a similar procedure as 2-[4-((S)-2-hydroxy-2-phenyl-ethylamino)-2-oxo-1,2-dihydro-pyridin-3-yl]-3H-benzoimidazole-4-carboxylic acid yielding 2-{4-[2-(3-chloro-phenyl)-ethylamino]-2-oxo-1,2-dihydro-pyridin-3-yl}-3H-benzoimidazole-4-carboxylic acid.

2-{4-[2-(3-chloro-phenyl)-ethylamino]-2-oxo-1,2-dihydro-pyridin-3-yl}-3H-benzoimidazole-4-carboxylic acid benzylamide was synthesized from 2-{4-[2-(3-chloro-phenyl)-ethylamino]-2-oxo-1,2-dihydro-pyridin-3-yl}-3H-benzoimidazole-4-carboxylic acid, benzylamine, DIEA, HATU and DMF using a similar procedure as 2-[4-((S)-2-hydroxy-2-phenyl-ethylamino)-2-oxo-1,2-dihydro-pyridin-3-yl]-3H- benzoimidazole-4-carboxylic acid 3-fluoro-benzylamide yielding 2-{4-[2-(3-chloro-phenyl)-ethylamino]-2-oxo-1,2-dihydro-pyridin-3-yl}-3H-benzoimidazole-4-carboxylic acid benzylamide. LC/MS calcd for $C_{28}H_{24}ClN_5O_2$ (m/e) 497.0, obsd 498 (M+H).

Example 5

2-{4-[2-(3-Chloro-phenyl)-ethylamino]-2-oxo-1,2-dihydro-pyridin-3-yl}-3H-benzoimidazole-4-carboxylic acid 4-fluoro-benzylamide

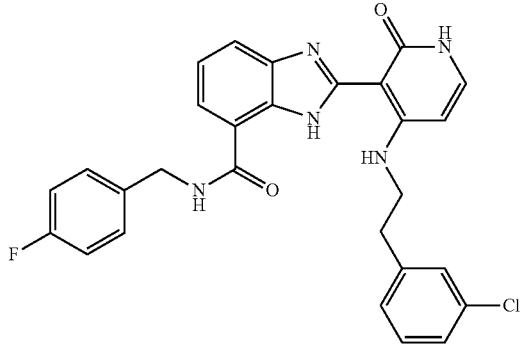 [SMILES: O=C(NCc1ccc(F)cc1)c1cccc2nc(-c3c(NCCc4cccc(Cl)c4)cc[nH]c3=O)[nH]c12]

2-{4-[2-(3-chloro-phenyl)-ethylamino]-2-oxo-1,2-dihydro-pyridin-3-yl}-3H-benzoimidazole-4-carboxylic acid 4-fluoro-benzylamide was synthesized from 2-{4-[2-(3-chloro-phenyl)-ethylamino]-2-oxo-1,2-dihydro-pyridin-3-yl}-3H-benzoimidazole-4-carboxylic acid, benzylamine, DIEA, HATU and DMF using a similar procedure as 2-[4-((S)-2-hydroxy-2-phenyl-ethylamino)-2-oxo-1,2-dihydro-pyridin-3-yl]-3H-benzoimidazole-4-carboxylic acid 3-fluoro-benzylamide yielding 2-{4-[2-(3-chloro-phenyl)-ethylamino]-2-oxo-1,2-dihydro-pyridin-3-yl}-3H-benzoimidazole-4-carboxylic acid 4-fluoro-benzylamide. LC/MS calcd for $C_{28}H_{23}ClFN_5O_2$ (m/e) 515.0, obsd 516 (M+H). $^1$H NMR (tautomers, DMSO-$d_6$) δ: 13.30-13.51 (m, 1H), 11.11-11.49 (m, 1H), 9.98-10.95 (m, 1H), 9.06-9.36 (m, 1H), 7.68-8.00 (m, 2H), 6.93-7.65 (m, 11H), 6.22 (d, J=7.3 Hz, 1H), 4.47-4.74 (m, 2H), 3.59-3.85 (m, 2H), 3.05 (t, J=6.9 Hz, 2H).

Example 6

Synthesis of 2-{4-[2-(3-Chloro-phenyl)-ethylamino]-2-oxo-1,2-dihydro-pyridin-3-yl}-3H-benzoimidazole-4-carboxylic acid 3-fluoro-benzylamide

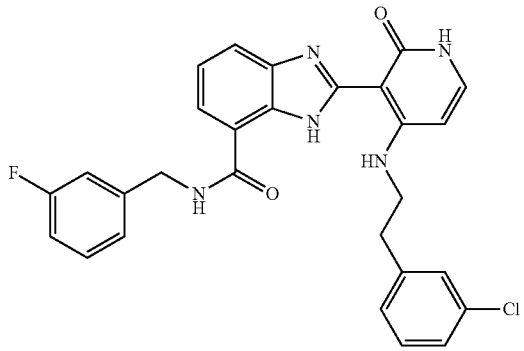 [SMILES: O=C(NCc1cccc(F)c1)c1cccc2nc(-c3c(NCCc4cccc(Cl)c4)cc[nH]c3=O)[nH]c12]

2-{4-[2-(3-chloro-phenyl)-ethylamino]-2-oxo-1,2-dihydro-pyridin-3-yl}-3H-benzoimidazole-4-carboxylic acid 3-fluoro-benzylamide was synthesized from 2-{4-[2-(3-chloro-phenyl)-ethylamino]-2-oxo-1,2-dihydro-pyridin-3-yl}-3H-benzoimidazole-4-carboxylic acid, benzylamine, DIEA, HATU and DMF using a similar procedure as 2-[4-((S)-2-hydroxy-2-phenyl-ethylamino)-2-oxo-1,2-dihydro-pyridin-3-yl]-3H-benzoimidazole-4-carboxylic acid 3-fluoro-benzylamide yielding 2-{4-[2-(3-chloro-phenyl)-ethylamino]-2-oxo-1,2-dihydro-pyridin-3-yl}-3H-benzoimidazole-3-carboxylic acid 4-fluoro-benzylamide. LC/MS calcd for $C_{28}H_{23}ClFN_5O_2$ (m/e) 515.0, obsd 516 (M+H). $^1$H NMR (tautomers, DMSO-$d_6$) δ: 13.42 (s, 1H), 11.15-11.46 (m, 1H), 10.00-10.91 (m, 1H), 9.08-9.41 (m, 1H), 7.69-8.00 (m, 2H), 6.98-7.59 (m, 11H), 6.22 (d, J=7.5 Hz, 1H), 4.49-4.78 (m, 2H), 3.63-3.82 (m, 2H), 3.05 (t, J=6.8 Hz, 2H).

Example 7

Synthesis of 2-{4-[2-(3-Chloro-phenyl)-ethylamino]-2-oxo-1,2-dihydro-pyridin-3-yl}-3H-benzoimidazole-4-carboxylic acid 2-fluoro-benzylamide

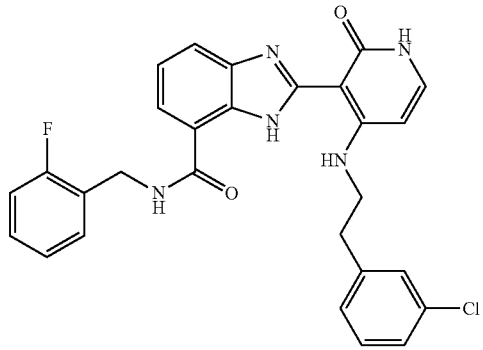 [SMILES: O=C(NCc1ccccc1F)c1cccc2nc(-c3c(NCCc4cccc(Cl)c4)cc[nH]c3=O)[nH]c12]

2-{4-[2-(3-chloro-phenyl)-ethylamino]-2-oxo-1,2-dihydro-pyridin-3-yl}-3H-benzoimidazole-4-carboxylic acid 2-fluoro-benzylamide was synthesized from 2-{4-[2-(3-chloro-phenyl)-ethylamino]-2-oxo-1,2-dihydro-pyridin-3-yl}-3H-benzoimidazole-4-carboxylic acid, benzylamine, DIEA, HATU and DMF using a similar procedure as 2-[4-((S)-2-hydroxy-2-phenyl-ethylamino)-2-oxo-1,2-dihydro-pyridin-3-yl]-3H-benzoimidazole-4-carboxylic acid 3-fluoro-benzylamide yielding 2-{4-[2-(3-chloro-phenyl)-ethylamino]-2-oxo-1,2-dihydro-pyridin-3-yl}-3H-benzoimidazole-4-carboxylic acid 2-fluoro-benzylamide. LC/MS calcd for $C_{28}H_{23}ClFN_5O_2$ (m/e) 515.0, obsd 516 (M+H). $^1$H NMR (tautomers, DMSO-$d_6$) δ: 13.33-13.49 (m, 1H), 11.14-11.45 (m, 1H), 10.05-10.92 (m, 1H), 9.08-9.32 (m, 1H), 7.70-7.98 (m, 2H), 7.02-7.61 (m, 11H), 6.16-6.32 (m, 1H), 4.53-4.80 (m, 2H), 3.43-3.84 (m, 2H), 2.75-3.12 (m, 2H).

The compounds of formula I possess valuable properties. It has been found that said compounds are useful in differentiating stem cells into more mature or adult-like hepatocytes for more accurate pharmaceutical testing and research. The activity of the present compounds in differentiating stem cells into more mature or adult-like hepatocytes is demonstrated by the following assays. In addition, the effect of the compounds of the present invention on host genes that led to cell susceptibility to HBV are also described.

In Vitro Testing with Human Induced Pluripotent Stem Cells

Human iPSC-derived hepatocytes (iCell® Hepatocytes) were exposed to the compounds of formula I with the goal of identifying conditions that favor greater functionality that better models the adult organ. High-throughput, microfluidic quantitative RT-PCR (qRT-PCR) was used to examine the expression of 32 genes that span a spectrum of hepatocyte functions that were either low or exhibited an immature phenotype in hiPSC-derived hepatocytes when compared to adult primary human hepatocytes. During the primary screen, multiple compounds were identified that resulted in a significant increase in a number of maturation-associated genes. Gene expression changes were validated and confirmed in a secondary screen, and functional consequences were queried.

Cells and Culture Conditions

Fresh iCell® Hepatocytes (day 20-23) were plated and cultured according to iCell Hepatocytes Dissociation and Plating User's Guide at 60 k cells per well in 96 well BIO Collagen IV coated plates (BD Cat#354429) 4 Hours post plating Medium C was removed and replaced with a 1:50 Matrigel (Cat#354227) overlay in Medium D. We dosed the cells at 5 uM in Medium D and 1% DMSO 24 hours post plating. Day 3, media was removed and we dosed again at 5 uM. Day 4 we Harvested RNA.

Gene Expression Profiling

Sample RNA was isolated using TaqMan® Gene Expression Cells-to-CT™ Kit (Life Technologies Cat#4387299) froze at −80 C at various time points post compound treatment. All samples were processed by microfluidic quantitative PCR using the Biomark Fluidigm 96.96 chips (BMK-M-96.96) and ABI Taqman probes. Normalization and model-based expression measurements were calculated using the Biogazelle qBASE and Genorm software. All sample data are the average of triplicates and normalized to 5 housekeeping genes for a relative gene expression value. Expression values are calculated by the fold change over vehicle control. See FIGS. 1 and 2.

Top compound hits were chosen based on a compound's ability to alter the gene expression in a manner predicted to increase cellular maturity, for instance an increase of adult specific markers or a decrease in fetal specific markers. For the secondary confirmation screen compound hits were chosen for a dose response on a broader panel of genes. We discovered that the compound of Example 1 caused the global increase of genes spanning hepatocyte function at multiple doses. (FIG. 1). Exposure to the compound of example 1 and five other structural analogs (Examples 2-7) results in the similar phenotypic change in iCell Hepatocytes based on gene expression of a panel of maturation-associated genes. (FIG. 2). The results in using the compound of Example 1 exhibited reproducible gene expression changes on 5+ independent batches of iCell Hepatocytes and is being further studied with the goal of identifying the mechanisms of action and functional consequences. Upon treatment with the compound of Example 1, iCell Hepatocytes are able to be infected in multiple genotypes of HBV and generate robust numbers of infected hepatocytes based on IHC and ELISA.

Microarray Analysis iCell Hepatocytes treated with the compound of example 1 results in the up and down-regulation of a host of genes; including a kinetic effect on interferon-stimulated gene (ISGs) expression. See FIGS. 15-I and 15-II, 16-I and 16-II and 18A-D and Table 1.

Purification of HBV from Serum

Two hundred microliters of HBV-containing serum was applied onto a 10-50% Optiprep gradient in SW41 tubes. Samples were centrifuged at 100,000×g for 2 hr at 4 C. Five hundred microliters fractions were collected from the top; each fraction was analyzed for HBsAg (ELISA) and HBV DNA (TaqMan PCR). Fractions containing virus were stored at −80 C. See FIGS. 13 and 14.

Infection of iCell Hepatocytes with HBV

Fresh iCell® Hepatocytes (day 20-23) were plated and cultured according to iCell Hepatocytes Dissociation and Plating User's Guide at 60 k cells per well in 96 well BIO Collagen IV coated plates (BD Cat#354429) 4 Hours post plating Medium C was removed and replaced with a 1:50 Matrigel (Cat#354227) overlay in Medium D. Twenty four hours post plating, cells were treated with 1 uM of the compound of example 1 in Medium D containing 1% DMSO. Media containing fresh compound was replenished 2 days later. At day 4 post plating, cells were infected with HBV at MOI (multiplicity of infection) of 10. Briefly, purified virus was diluted in medium D containing the compound of example 1 and incubated with cells for 4-6 hr or overnight. After removal of virus inoculum, fresh media containing 1 uM of the compound of example 1 was added and cells were incubated for 14 days with a medium change every 2 days. Culture media were analyzed for secreted viral antigens (HBsAg, HBeAg) and HBV DNA. See FIGS. 3, 4, 5 and 6.

Taken together, the data shows that using the compounds of formula I as endogenous signals provides a rapid, efficient, nongenetic and cost-effective means to modulate iCell Hepatocyte functionality. The generation of iCell Hepatocytes infected with HBV using the compounds of formula I provides a method for basic virology and drug discovery. Small molecule library screens for the functional improvement of stem cell derived cells may lead to a new generation of in vitro assays for drug discovery.

The invention claimed is:

1. A method for differentiating stem cells into hepatocytes comprising administering to said stem cells a compound of formula I:

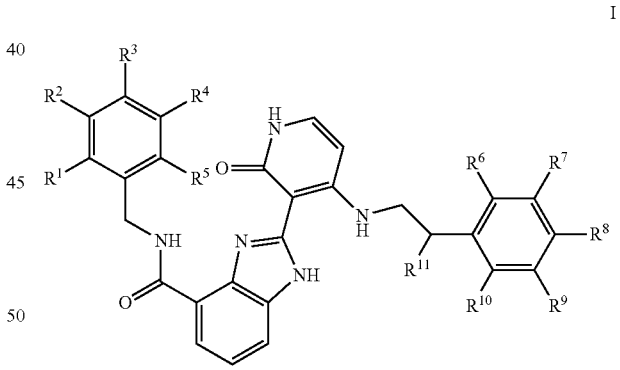

or a pharmaceutically acceptable salt or ester thereof; wherein $R^1$, $R^2$, $R^3$, $R^4$, $R^5$, $R^6$, $R^7$, $R^8$, $R^9$, and $R^{10}$ are independently hydrogen or halogen; and $R^{11}$ is hydrogen or hydroxy.

2. A method according to claim 1, wherein the hepatocytes are infected with Hepatitis B virus.

3. A method according to claim 2, wherein the infected hepatocytes are used to screen compounds to treat Hepatitis B virus.

4. A method according to claim 1, wherein interferon-stimulated genes are down regulated in differentiated hepatocytes.

5. A method according to claim 4, wherein said hepatocytes are infected with Hepatitis B virus.

6. A method according to claim 2, wherein the Hepatitis B virus is a patient-derived Hepatitis B virus and not a cell culture-derive Hepatitis B virus.

7. A method according to claim 1, wherein the cells are infected with a substantially pure population of Dane particles.

8. The method according to claim 1, wherein said compound is 2-[4-((S)-2-hydroxy-2-phenyl-ethylamino)-2-oxo-1,2-dihydro-pyridin-3-yl]-3H-benzoimidazole-4-carboxylic acid 3-fluoro-benzylamide.

\* \* \* \* \*